US012810998B2

(12) United States Patent
Qiu et al.

(10) Patent No.: US 12,810,998 B2
(45) Date of Patent: Nov. 24, 2026

(54) TECHNIQUE FOR RENDERING A SHEARED-VOLUME BASED MEDICAL IMAGE

(71) Applicant: Siemens Healthineers AG, Forchheim (DE)

(72) Inventors: Feng Qiu, Pennington, NJ (US); Lining Yang, East Windsor, NJ (US)

(73) Assignee: Siemens Healthineers AG, Forchheim (DE)

( * ) Notice: Subject to any disclaimer, the term of this patent is extended or adjusted under 35 U.S.C. 154(b) by 337 days.

(21) Appl. No.: 18/604,901

(22) Filed: Mar. 14, 2024

(65) Prior Publication Data

US 2024/0339198 A1 Oct. 10, 2024

(30) Foreign Application Priority Data

Mar. 28, 2023 (EP) .................................... 23164679

(51) Int. Cl.

| | |
|---|---|
| ***G06V 10/46*** | (2022.01) |
| ***G06T 7/11*** | (2017.01) |
| ***G06T 15/06*** | (2011.01) |
| ***G16H 30/20*** | (2018.01) |
| ***G16H 30/40*** | (2018.01) |

(52) U.S. Cl.

CPC ............... *G16H 30/40* (2018.01); *G06T 7/11* (2017.01); *G06T 15/06* (2013.01); *G06V 10/46* (2022.01); *G16H 30/20* (2018.01); *G06T 2207/10072* (2013.01)

(58) Field of Classification Search

None

See application file for complete search history.

(56) References Cited

U.S. PATENT DOCUMENTS

2004/0204644 A1* 10/2004 Tsougarakis ............ B23P 19/00 324/309

2008/0246768 A1* 10/2008 Murray .................. G06T 15/08 345/427

2018/0357814 A1* 12/2018 Bohn ...................... G06T 15/08

OTHER PUBLICATIONS

Zuiderveld Karel J et al: “Acceleration of ray-casting using 3D distance transforms”, Jan. 1, 1992 (Jan. 1, 1992), pp. 1-12; Retrieved from the Internet: URL: https://www.spiedigitallibrary.org/conference-proceedings-of-spie/1808/1/Acceleration-of-ray-casting-using-3-D-distance-transforms/10.1117/12.131088.full.

Felzenszwalb, Pedro F., and Daniel P. Huttenlocher. “Distance transforms of sampled functions.” Theory of computing 8.1 (2012): 415-428.

(Continued)

*Primary Examiner* — Anh-Tuan V Nguyen

(57) ABSTRACT

A medical image associated with a volumetric medical dataset including a sheared volume, which dataset is received from a medical scanner, is rendered. The sheared volume is a series of 2D slices and a sheared direction. An auxiliary rectilinear volume is constructed such that the 2D slices are preserved, albeit with displaced 2D lattice, and the sheared direction is replaced by a direction orthogonal to the 2D slices. Nearest points on the sheared and the auxiliary rectilinear 3D lattices are determined. A value of a (e.g., binary) scalar field at a point on the sheared 3D lattice is assigned to the nearest point on the auxiliary rectilinear 3D lattice, where a Euclidean distance transform (EDT) is applied to the value of the scalar field. Based on the EDT value of the scalar field, the medical image is rendered.

17 Claims, 8 Drawing Sheets

(56) References Cited

OTHER PUBLICATIONS

Kim, Changhwan, et al. "An additional tilted-scan-based CT metal-artifact-reduction method for radiation therapy planning." Journal of applied clinical medical physics 20.1 (2019): 237-249.
Kim, Keun Ho, et al. "Fast surface and volume rendering based on shear-warp factorization for a surgical simulator." Computer Aided Surgery 7.5 (2002): 268-278.
Lacroute, Philippe, and Marc Levoy. "Fast volume rendering using a shear-warp factorization of the viewing transformation." Proceedings of the 21st annual conference on Computer graphics and interactive techniques. 1994. pp. 451-458.
Philip Rideout, Distance Fields, https://prideout.net/blog/distance_fields/, 2018. pp. 1-10.
Extended European Search Report (EESR) mailed Sep. 4, 2023 in corresponding European Patent Application No. 23164679.5.

* cited by examiner

TECHNIQUE FOR RENDERING A SHEARED-VOLUME BASED MEDICAL IMAGE

RELATED APPLICATION

This application claims the benefit of EP 23164679.5, filed on Mar. 28, 2023, which is hereby incorporated by reference in its entirety.

BACKGROUND

Signed distance fields (SDFs) have many applications to volume data processing, rendering, and computer vision. For example, FIG. 3 shows smooth contours extracted from the SDFs of a segmented heart binary image dataset (image).

Contours extracted directly from a binary image (and/or a binary volume) are not smooth because the underlying binary image is not smooth. The algorithm to calculate the SDF from a binary two-dimensional (2D) image or three-dimensional (3D) volume is conventionally called signed distance transform (SDT). For general images (and/or volumes), it has been demonstrated that the Euclidean SDT (where the distance is the Euclidean distance) can be solved in linear time. However, the conventional method can only process images (and/or volumes) on a regular (and/or rectilinear) grid.

Depending on the type of medical examination or treatment, it is not possible or is inappropriate to obtain images or volumes on regular grids. Sheared volumes arise, e.g., in procedures with optical guidance for a medical instrument, such as a needle. Examples of such procedures are biopsy and drainage. Sheared volumes also arise if there is a need to reduce radiation on a particularly sensitive anatomical structure, such as a patient's eye. For such cases with sheared volume imaging, the conventional methods of determining Euclidean distance transforms (EDTs) and SDTs cannot be used, impeding a faithful and/or real-time rendering pipeline for the acquired medical image datasets.

It is therefore an object to provide a solution for enabling, in particular real-time, rendering of medical images based on volumetric medical datasets with sheared volumes. Alternatively, or in addition, it is an object to provide a technique for determining an Euclidean distance transform (EDT), and/or a signed distance field (SDF) for a volumetric medical dataset with a sheared volume, and/or to accelerate the rendering of images based on sheared volume data, in particular while saving computing resources.

SUMMARY AND DESCRIPTION

This object is solved by a method for rendering a medical image associated with a volumetric medical dataset, by a computing device, by a system, by a computer program (also: computer program product), and by a non-transitory computer-readable medium. Advantageous aspects, features and embodiments are described in the following description.

In the following, the solution is described with respect to the method for rendering a medical image associated with a volumetric medical dataset as well as with respect to the computing device. Features, advantages or alternative embodiments herein can be assigned to the other objects (e.g., the system, the computer program or a computer program product), and vice versa. In other words, claims for the computing device, and/or the system, can be improved with features described or claimed in the context of the method. In this case, the functional features of the method are embodied by structural units (and/or modules) of the computing device or system and vice versa, respectively.

As to a first aspect, a computer-implemented method for rendering a medical image associated with a volumetric medical dataset including a sheared volume is provided. The method includes an act of receiving a volumetric medical dataset from a medical scanner. The medical scanner provides the volumetric medical dataset according to a sheared volume. The sheared volume is represented by a sheared three-dimensional (3D) lattice including a series of parallel rectilinear two-dimensional (2D) lattices and a series of parallel sheared one-dimensional (1D) lattices. Each sheared 1D lattice is non-orthogonal to a 2D plane (which may also be denoted as slice) spanned by any one of the 2D lattices. Each lattice point of the sheared 3D lattice represents a voxel of the volumetric medical dataset. A (e.g., binary) value of a scalar field is associated with the voxel.

The method further includes an act of constructing an auxiliary rectilinear volume represented by an auxiliary rectilinear 3D lattice. The auxiliary rectilinear volume includes (and/or tightly bounds, in particular from the outside) the sheared volume of the received volumetric medical dataset. A series of auxiliary rectilinear 2D lattices of the auxiliary rectilinear 3D lattice spans the same series of 2D planes as the series of 2D lattice of the sheared 3D lattice with identical 2D lattice constants of the auxiliary rectilinear 2D lattices and the 2D lattice of the sheared 3D lattice. A series of auxiliary 1D lattices of the auxiliary rectilinear 3D lattice is orthogonal to the 2D planes spanned by the 2D lattices. The lattice constant of the auxiliary 1D lattice is determined as the distance between neighboring (also denoted as consecutive) 2D planes. Neighboring (also: consecutive) 2D planes are specified by passing through neighboring (also: consecutive) lattice points along the sheared 1D lattice.

The method may further include an act of determining, for any lattice point of the sheared 3D lattice, the nearest lattice point on the constructed auxiliary rectilinear 3D lattice. Determining the nearest lattice point may include determining a coordinate distance between the lattice point of the sheared 3D lattice and any lattice point on the constructed auxiliary rectilinear 3D lattice and selecting the lattice point with the minimal coordinate distance, to the lattice point of the sheared 3D lattice, among the lattice points on the constructed auxiliary rectilinear 3D lattice.

Alternatively, or in addition, the method may include an act of determining, for any lattice point of the constructed auxiliary rectilinear 3D lattice, the nearest lattice point on the sheared 3D lattice. Determining the nearest lattice point may include determining a coordinate distance between the lattice point of the constructed auxiliary rectilinear 3D lattice and any lattice point on the sheared 3D lattice and selecting the lattice point with the minimal coordinate distance, to the lattice point of the constructed auxiliary rectilinear 3D lattice, among the lattice points on the sheared 3D lattice.

The method further includes an act of assigning, to any lattice point of the sheared 3D lattice, the value of the scalar field of the lattice point of the sheared 3D lattice to the determined nearest lattice point on the constructed auxiliary rectilinear 3D lattice.

The method further includes an act of applying, for any lattice point of the constructed auxiliary rectilinear 3D lattice, a Euclidean distance transform (EDT) to the value of the scalar field assigned to the lattice point of the constructed auxiliary rectilinear 3D lattice and obtaining an (e.g., associated) EDT value of the scalar field.

The method may further include an act of assigning, to any lattice point of the sheared 3D lattice, the obtained (e.g., associated) EDT value of the scalar field of the determined nearest lattice point on the constructed auxiliary rectilinear 3D lattice.

The method still further includes an act of rendering a medical image based on the assigned (e.g., obtained and/or associated) EDT values (e.g., of the sheared volume).

By the technique, constructing a medical image for display from a volumetric medical dataset (which may also be denoted as 3D medical image), which is provided by a medical scanner (e.g., a magnetic resonance imaging, MRI, scanner and/or a computed tomography, CT, scanner) according to a sheared volume (which may also be denoted as sheared model matrix), may be improved in terms of quality (e.g., of the medical image) and/or efficiency, e.g., including time and/or computing resources (e.g., including memory and/or processing power). Alternatively, or in addition, the method may enable real-time applications and/or accelerated rendering, e.g., for optical guidance during a needle procedure. E.g., acquiring the volumetric medical dataset according to a sheared volume may be required to enable the handling of the needle.

A needle procedure may include a biopsy and/or drainage. The needle procedure may be performed while the medical scanner continues acquiring volumetric medical datasets, from which, according to the technique, medical images are constructed and displayed for optical guidance.

Alternatively, or in addition, the medical scanner may provide the volumetric medical dataset according to the sheared volume in order to reduce radiation on sensitive anatomical structures (e.g., a patient's eyes).

The medical scanner may be used for a medical scan. A medical scan may be performed on a human body (briefly: body), and/or a (in particular human) patient.

Further alternatively, or in addition, by the technique, a Signed Distance Transform (SDT) for a gantry-tilted volume may be determined. The SDT can be used for accurate, and/or faithful, in particular real-time, rendering of a medical image captured by a tilted gantry, e.g., of a CT scan.

The SDT of a scalar field may also be denoted as signed distance function (SDF).

The rectilinear 2D lattice (also denoted as non-auxiliary rectilinear 2D lattice, real rectilinear 2D lattice or actual rectilinear 2D lattice, and/or as rectangular 2D lattice) of the sheared (also: oblique) volume may be spanned by a first coordinate (e.g., x) and a second coordinate (e.g., y). The axes of the first coordinate (e.g., x) and of the second coordinate (e.g., y) may be orthogonal.

The sheared (also: oblique) 1D lattice may be spanned by a third coordinate (e.g., z). The axis of the third coordinate (e.g., z) may be non-orthogonal, and/or at an oblique angle, to the 2D plane (also: slice) spanned by the rectilinear 2D lattice of the sheared volume.

The sheared (also: oblique) 3D lattice may correspond to a series of parallelly displaced (also: parallel) rectilinear 2D lattices, wherein the parallel displacement is based on the sheared 1D lattice. Alternatively, or in addition, the sheared 3D lattice may include the series of parallelly displaced 2D lattices and the series of parallelly displaced (also: parallel) sheared 1D lattices, with each 2D lattice sharing exactly one lattice point with each of the sheared 1D lattices, and vice versa.

The auxiliary rectilinear 2D lattice of the auxiliary rectilinear volume may be spanned by an auxiliary first coordinate (e.g., x') and an auxiliary second coordinate (e.g., y'). The axes of the auxiliary first coordinate (e.g., x') and of the auxiliary second coordinate (e.g., y') may be orthogonal. Alternatively, or in addition, the axis of the auxiliary first coordinate (e.g., x') may be parallel to the axis of the (e.g., non-auxiliary, and/or real) first coordinate (e.g., x), and/or the axis of the auxiliary second coordinate (e.g., y') may be parallel to the axis of the (e.g., non-auxiliary, and/or real) second coordinate (e.g., y).

The auxiliary 1D lattice may by spanned by an auxiliary third coordinate (e.g., z'). The axis of the auxiliary third coordinate (e.g., z') may be perpendicular (and/or orthogonal) to the 2D plane spanned by the (e.g., auxiliary) rectilinear 2D lattice. Alternatively, or in addition, the direction of the axis of the auxiliary third coordinate (e.g., z') may be determined by the cross product (also denoted as vector product) of the vectors spanning the axes of the (e.g., auxiliary) first and second coordinates (e.g., x' and y'; equivalently also x and y may be used as the axes of the corresponding non-auxiliary and auxiliary rectilinear 2D lattices are parallel).

The auxiliary rectilinear 3D lattice may correspond to a series of parallelly displaced (also: parallel) rectilinear 2D lattices, wherein the parallel displacement is based on the auxiliary 1D lattice. Alternatively, or in addition, the auxiliary rectilinear 3D lattice may include a series of parallelly displaced auxiliary rectilinear 2D lattices and a series of parallelly displaced (also: parallel) auxiliary 1D lattices, with each auxiliary rectilinear 2D lattice sharing exactly one lattice point with each of the auxiliary 1D lattices, and vice versa.

A 2D plane spanned by a (e.g., non-auxiliary and/or auxiliary) 2D lattice may also be denoted as 2D slice (or briefly: slice).

The lattice constant may also be denoted as length scale (e.g., of the corresponding coordinate direction of the lattice). Alternatively, or in addition, the lattice constant may denote the distance between neighboring voxels along the corresponding coordinate direction.

The auxiliary rectilinear volume may tightly bound the sheared volume (e.g., from the outside). E.g., the non-auxiliary 2D lattice and the auxiliary 2D lattice at one side of the sheared volume and the auxiliary rectilinear volume may be aligned (and/or the auxiliary 2D lattice at that side may include the non-auxiliary 2D lattice, in particular without any parallel displacement). Alternatively, or in addition, the auxiliary rectilinear volume may be represented by the smallest (e.g., in terms of the number of lattice points and/or overall lengths along any one of the coordinate axes, in particular along the first and/or second auxiliary coordinate axes) auxiliary 3D lattice, into which the sheared volume (and/or the sheared 3D lattice representing the sheared volume) may be inset (and/or fit).

The scalar field may include a binary field (also denoted as Boolean field), e.g., distinguishing between foreground (e.g., any organ) and background per voxel. The binary field may alternatively include the values "true" (T) and "false" (F), e.g., for foreground and background per voxel, respectively.

Alternatively, or in addition, the scalar field may be a k-ary field. E.g., the scalar field may be a different value for each of a number of different (e.g., types of) organs and another value for the background. E.g., the values 0, 1, 2, . . . , k−1 may be assigned to the voxel representing background, liver, kidney, and so on, for k−1 different organs.

Alternatively, or in addition, a heart segmentation (e.g., for a CT scan) may include a scalar field with several (e.g., nine) values. E.g., the scalar values 0, 1, 2, . . . , 8 may represent the left ventricle (LV) blood pool, LV myocardium, LV other structure, LV endocardium, LV epicardium, left atrium (LA), right atrium (RA), right ventricle (RV), and aorta (AO), respectively.

According to an embodiment, the technique may be extended to a scalar field storing floating point values (e.g., in relation to a flow velocity).

The (e.g., squared) EDT of a (e.g., binary) scalar field may include a scalar field with zero and any natural number as values.

It is noted that in the following, the EDT, and/or ED, predominantly refer to (e.g., binary) scalar fields, and/or values, without squaring. However, whenever evident from the context, EDT, and/or ED, may also loosely be used to refer to the squares of the (e.g., binary) scalar fields, and/or values.

The EDT for a binary scalar field may indicate the (e.g., minimal) Euclidean distance of a voxel with a first predetermined value of the scalar field (e.g., "false" or "background") from a (e.g., nearest) voxel with a second predetermined value of the scalar field (e.g., "true" or "foreground").

Alternatively, or in addition, the EDT of the binary scalar field may be determined by determining a squared Euclidean distance (ED). The squared ED may be determined based on a series of overlapping quadratic parabolas. The shape of any one of the quadratic parabolas may depend on the lattice constant of the corresponding lattice direction. The squared ED may be determined by first determining the squared ED per row, and/or per column, of a matrix (e.g., representing pixels, and/or voxels), performing sums of squared EDs of rows and columns and determining the minimum of all sums. The rows and columns of the matrix may correspond to the lattice points of a rectilinear, e.g., D2, lattice.

The act of applying the EDT may include applying a Signed EDT (SDT). The SDT may correspond to the EDT for any voxel with a first predetermined value. For any voxel with the second predetermined (in particular differing from the first predetermined) value, the SDT may include the negative (and/or inverse) of the analogously computed EDT.

Alternatively, or in addition, the (e.g., squared) SDT of a (e.g., binary) scalar field may include any integer value. Positive values may correspond to the (e.g., minimal) Euclidean distance of a voxel with a first predetermined value of the scalar field (e.g., "false" or "background") from a (e.g., nearest) voxel with a second predetermined value of the scalar field (e.g., "true" or "foreground"). Alternatively, or in addition, negative values may correspond to the (e.g., minimal) Euclidean distance of a voxel with the second predetermined value (e.g., "true" or "foreground") from a (e.g., nearest) voxel with the first predetermined value of the scalar field (e.g., "false" or "background"). Alternatively, or in addition, the above considerations may apply with the opposite sign, i.e., with positive values and negative values exchanged.

In any example, the first predetermined value of the scalar field may be different (e.g., the opposite) than the second predetermined value of the scalar field.

The displaying may include, and/or may be performed by, a display device (briefly also: display), in particular a screen (e.g., located in an operating theatre and/or in a doctor's office), and/or an extended reality (XR) headset. XR may include virtual reality (VR) and/or augmented reality (AR).

The output to the display device may include a wired and/or wireless transmission of the constructed medical image.

Alternatively, or in addition, the medical image may be projected, e.g., directly, onto a patient, e.g., by an extended reality (XR) device (in particular an XR headset). The XR may include, and/or may be an umbrella term for, augmented reality (AR), and/or virtual reality (VR). The projected medical image may be rendered using the technique, in particular using a signed distance field (SDF) determined by the technique.

The act of determining, for any lattice point of the sheared 3D lattice, the nearest lattice point on the constructed auxiliary rectilinear 3D lattice may include applying a Voronoi map.

A Voronoi map may be defined as and/or may include a function that can return the nearest point in a field with predetermined scalar value to an input point. Alternatively, or in addition, the closest point transform (CPT) may be a 3D discrete version of a Voronoi map, where all the points are located on a 3D lattice. The SDF can be deducted from the closest point transform (CPT) with point coordinates.

The series of rectilinear 2D lattices may include a series of square 2D lattices.

A square 2D lattice (briefly: square lattice) may also be denoted as quadratic 2D lattice (briefly: quadratic lattice). Alternatively, or in addition, the two lattice constants of the rectilinear 2D lattice may be equal (and/or identical).

The scalar field associated with the voxel may include a binary field. Alternatively, or in addition, the scalar field associated with the voxel may include a k-ary field with k a natural number greater than, or equal to, two.

The volumetric medical dataset may include binary data (and/or the binary field), and/or k-ary data (and/or the k-ary field) for a natural number k of at least two, per voxel.

The binary data may also be denoted as Boolean data. Alternatively, or in addition, the binary field may also be denoted as Boolean field.

The binary, and/or k-ary, data may include a classification. E.g., the binary data may include a "True" or "False" classification. Alternatively, or in addition, the binary data may include a classification as anatomical structure, in particular as an organ, or as background. Further alternatively, or in addition, the k-ary data may include a classification according to a type of anatomical structure, in particular a type of organ, or a classification as background.

The act of applying the EDT to the value of the scalar field associated with the voxel represented by the lattice point may include applying a signed EDT (SDT). Alternatively, or in addition, the sign of the signed Euclidean distance transformed scalar field (briefly: signed EDT scalar field; also: SDT scalar field) at the voxel may be based on the value of the scalar field at the voxel in the received volumetric medical dataset.

For a binary scalar field, the Euclidean distance transformed scalar field (also: Euclidean distance, ED) may be positive at any voxel having a first value of the binary scalar field and/or negative at any voxel having a second value (in particular different from the first value) of the binary scalar field.

The signed Euclidean distance transformed scalar field may also be denoted as signed distance field (SDF).

The signed distance field (SDF) may also be denoted as signed distance function, or shortly as distance field. Alternatively, or in addition, the SDF may include a position as an input and may output a distance from the position to a nearest part of a shape (e.g., segmented organ and/or vessel and/or medical instrument and/or body, or part thereof). Further alternatively, or in addition, the SDF may include a subtraction of an inverted Euclidean distance transform (EDT) from an original EDT. Still further alternatively, or in addition, a negative value of the output of the SDF may correspond to a position inside a contour of the shape and a positive value of the output of the SDF corresponds to a position outside the contour of the shape, or vice versa.

The act of applying the EDT, and/or the SDT, to the value of the scalar field associated with the voxel represented by the lattice point may include a closest point transform (CPT).

The CPT may include storing (and/or saving) the coordinates of the nearest lattice point on the (e.g., non-auxiliary) rectilinear 2D lattice according to a coordinate system of the auxiliary rectilinear 2D lattice lying within the same 2D plane (e.g., as the 2D plane spanned by the non-auxiliary rectilinear 2D lattice).

The value of the scalar field associated with the voxel of the received volumetric medical dataset may be indicative of an anatomical structure.

The classification of the anatomical structure may include a type of organ, a type of (e.g., soft and/or hard) tissue, and/or a background.

The rendered medical image may include a contour of an anatomical structure. Alternatively, or in addition, the rendered medical image may include a segmentation of an anatomical structure. Further alternatively, or in addition, the rendered medical image may include a volume representation of an anatomical structure.

The volumetric medical data set (which may also be denoted as input) may, according to the technique, include a 3D k-ary value volume (and/or a volume with k-ary values of a scalar field) that represents a segmentation of anatomical structures, e.g., left atrium (LA), right atrium (RA), and/or any further anatomical structure of the heart. The segmentation volume may be generated from a 3D volume output from a medical scanner, which may also be denoted as scanning device (e.g., a CT scanner, and/or an MRI scanner), or briefly scanner. While displaying a medical image on the display device, and/or by the XR device, the medical image may be displaying (and/or showing) a multiplanar reformatted (MPR) image, and/or one slice of the volume and a contour of the segmented anatomical structure. To obtain the contour, the technique may be used to determine (e.g., calculate) the SDF from the segmentation volume efficiently (and/or quickly) and use the SDF to render the contour.

The act of rendering the medical image may include performing a ray tracing algorithm. Optionally, the ray tracing algorithm may use, based on the EDT value of the scalar field, empty space skipping.

The method may further include an act of outputting the rendered medical image for display.

The medical scanner (which may also be denoted as medical imaging device) may include a computed tomography (CT) scanner. Alternatively, or in addition, the medical scanner may include a magnetic resonance imaging (MRI) scanner. Alternatively, or in addition, the medical scanner may include an ultrasound (US) scanner. Alternatively, or in addition, the medical scanner may include a positron emission tomography (PET) scanner. Further alternatively, or in addition, the medical scanner may include a single-photon emission tomography (SPECT) scanner.

The medical scanner may include a gantry. The received volumetric medical dataset may include a sheared volume according to an oblique position of the gantry, e.g., relative to a patient table. The patient table may also be denoted as operating table, examination table, and/or patient bench.

The method may be used for optical guidance by the medical scanner during an, in particular oblique, needle procedure. Optionally, the needle procedure may include performing a biopsy and/or a drainage.

As to a device aspect, a computing device for rendering a medical image associated with a volumetric medical dataset including a sheared volume is provided. The computing device includes a volumetric medical dataset receiving interface configured for receiving a volumetric medical dataset from a medical scanner. The medical scanner provides the volumetric medical dataset according to a sheared volume. The sheared volume is represented by a sheared 3D lattice including a series of parallel rectilinear 2D lattices and a series of parallel sheared 1D lattices. Each sheared 1D lattice is non-orthogonal to a 2D plane spanned by any one of the 2D lattices. Each lattice point of the sheared 3D lattice represents a voxel of the volumetric medical dataset. A (e.g., binary) value of a scalar field is associated with the voxel.

The computing device further includes an auxiliary rectilinear constructing module implemented by a processor configured for constructing an auxiliary rectilinear volume represented by an auxiliary rectilinear 3D lattice. The auxiliary rectilinear volume includes the sheared volume of the received volumetric medical dataset. A series of auxiliary rectilinear 2D lattices of the auxiliary rectilinear 3D lattice spans the same series of 2D planes as the series of 2D lattice of the sheared 3D lattice with identical 2D lattice constants of the auxiliary rectilinear 2D lattices and the 2D lattice of the sheared 3D lattice. A series of auxiliary 1D lattices of the auxiliary rectilinear 3D lattice is orthogonal to the 2D planes spanned by the 2D lattices. The lattice constant of the auxiliary 1D lattice is determined as the distance between neighboring 2D planes. The neighboring 2D planes are specified by passing through neighboring lattice points along the sheared 1D lattice.

The computing device further includes a determining module implemented by a processor configured for determining, for any lattice point of the sheared 3D lattice, the nearest lattice point on the constructed auxiliary rectilinear 3D lattice, or vice versa. Determining the nearest lattice point may include determining a coordinate distance between the lattice point of the sheared 3D lattice and any lattice point on the constructed auxiliary rectilinear 3D lattice and selecting the lattice point with the minimal coordinate distance, to the lattice point of the sheared 3D lattice, among the lattice points on the constructed auxiliary rectilinear 3D lattice. Alternatively, or in addition, determining the nearest lattice point may include determining a coordinate distance between the lattice point of the constructed auxiliary rectilinear 3D lattice and any lattice point on the sheared 3D lattice and selecting the lattice point with the minimal coordinate distance, to the lattice point of the constructed auxiliary rectilinear 3D lattice, among the lattice points on the sheared 3D lattice.

The computing device further includes a first assigning module implemented by a processor configured for assigning, to any lattice point of the sheared 3D lattice, the value of the scalar field of the lattice point of the sheared 3D lattice to the determined nearest lattice point on the constructed auxiliary rectilinear 3D lattice.

The computing device further includes an applying module implemented by a processor configured for applying, to any lattice point of the constructed auxiliary rectilinear 3D lattice, an EDT to the value of the scalar field assigned to the lattice point of the constructed auxiliary rectilinear 3D lattice. The applying module may be further configured for obtaining an associated EDT value of the scalar field.

Alternatively, or in addition, the obtaining of an associated EDT value of the scalar field may be configured to be performed by a (e.g., separate) obtaining module.

The computing device may further include a second assigning module implemented by a processor configured for assigning, to any lattice point of the sheared 3D lattice, the obtained EDT value of the scalar field of the determined nearest lattice point on the constructed auxiliary rectilinear 3D lattice.

The computing device still further includes a rendering module implemented by a processor configured for rendering a medical image based on the (e.g., assigned, obtained and/or associated) EDT values (e.g., of the sheared volume).

The computing device may be configured to perform the method according to the method aspect.

As to a system aspect, a system for rendering a medical image associated with a volumetric medical dataset including a sheared volume is provided. The system includes a computing device according to the device aspect. The system further includes one or more medical scanners configured to provide a volumetric medical dataset to the (in particular volumetric medical dataset receiving interface of the) computing device. The system still further includes a display device configured to receive the rendered medical image from the (in particular rendering module of the) computing device. Alternatively, or in addition, the display device is configured for displaying the rendered medical image.

The system may be configured to perform the method according to the method aspect.

As to a further aspect, a computer program product including program elements is provided. The program elements induce a computing device to carry out the acts of the method, according to the method aspect, for rendering a medical image associated with a volumetric medical dataset including a sheared volume, when the program elements are loaded into a memory of the computing device.

As to a still further aspect, a non-transitory computer-readable medium is provided. On the computer-readable medium, program elements are stored that can be read and executed by a computing device, in order to perform acts of the method, according to the method aspect, for rendering a medical image associated with a volumetric medical dataset including a sheared volume, when the program elements are executed by the computing device.

The properties, features and advantages of this invention described above, as well as the manner they are achieved, become clearer and more understandable in the light of the following description and embodiments, which will be described in more detail in the context of the drawings. This following description does not limit the invention on the contained embodiments. Same components or parts can be labeled with the same reference signs in different figures. In general, the figures are not for scale.

It shall be understood that a preferred embodiment of the present invention can also be any combination of the dependent claims or above embodiments with the respective independent claim.

These and other aspects of the invention will be apparent from and elucidated with reference to the embodiments described hereinafter.

Any reference signs in the claims should not be construed as limiting the scope.

DETAILED DESCRIPTION

Figure 1:
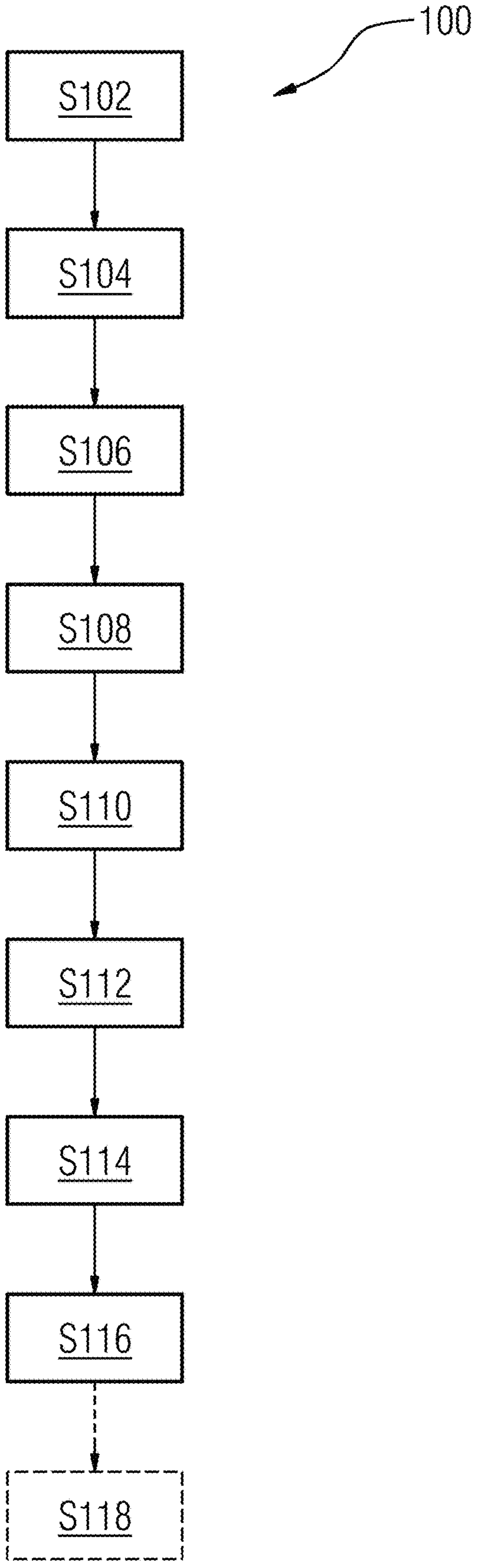
FIG. 1 is a flow chart of a method for rendering a medical image associated with a volumetric medical dataset including a sheared volume according to a preferred embodiment.

FIG. 1 schematically illustrates an example of a computer-implemented method for rendering a medical image associated with a volumetric medical dataset including a sheared volume. The method is generally referred to by the reference sign 100.

The method 100 includes an act S102 of receiving a volumetric medical dataset from a medical scanner. The medical scanner provides the volumetric medical dataset according to a sheared volume. The sheared volume is represented by a sheared three-dimensional (3D) lattice including a series of parallel rectilinear two-dimensional (2D) lattices and a series of parallel sheared one-dimensional (1D) lattices. Each sheared 1D lattice is non-orthogonal to a 2D plane spanned by any one of the 2D lattices. Each lattice point of the sheared 3D lattice represents a voxel of the volumetric medical dataset. A value of a (e.g., binary) scalar field is associated with the voxel.

The method 100 further includes an act S104 of constructing an auxiliary rectilinear volume represented by an auxiliary rectilinear 3D lattice. The auxiliary rectilinear volume includes the sheared volume of the received S102 volumetric medical dataset. A series of auxiliary rectilinear 2D lattices of the auxiliary rectilinear 3D lattice spans the same series of 2D planes as the series of 2D lattice of the sheared 3D lattice with identical 2D lattice constants of the auxiliary rectilinear 2D lattices and the 2D lattice of the sheared 3D lattice. A series of auxiliary 1D lattices of the auxiliary rectilinear 3D lattice is orthogonal to the 2D planes spanned by the 2D lattices. The lattice constant of the auxiliary 1D lattice is determined as the distance between neighboring 2D planes. Neighboring 2D planes are specified by passing through neighboring lattice points along the sheared 1D lattice.

The method 100 further includes an act S106 of determining, for any lattice point of the sheared 3D lattice, the nearest lattice point on the constructed S104 auxiliary rectilinear 3D lattice, or vice versa. Determining S106 the nearest lattice point may include determining a coordinate distance between the lattice point of the sheared 3D lattice and any lattice point on the constructed S104 auxiliary rectilinear 3D lattice and selecting the lattice point with the minimal coordinate distance, to the lattice point of the sheared 3D lattice, among the lattice points on the constructed S104 auxiliary rectilinear 3D lattice. Alternatively, or in addition, determining S106 the nearest lattice point may include determining a coordinate distance between the lattice point of the constructed S104 auxiliary rectilinear 3D lattice and any lattice point on the sheared 3D lattice and selecting the lattice point with the minimal coordinate distance, to the lattice point of the constructed S104 auxiliary rectilinear 3D lattice, among the lattice points on the sheared 3D lattice.

The method 100 further includes an act S108 of assigning, to any lattice point of the sheared 3D lattice, the value of the scalar field of the lattice point of the sheared 3D lattice of the determined S106 nearest lattice point on the constructed S104 auxiliary rectilinear 3D lattice.

The method 100 further includes an act S110 of applying, for any lattice point of the constructed S104 auxiliary rectilinear 3D lattice, a Euclidean distance transform (EDT) to the value of the scalar field assigned S108 to the lattice point of the constructed S104 auxiliary rectilinear 3D lattice.

The method 100 further includes an act S112 of obtaining an associated EDT value of the scalar field.

The method 100 may further include an act S114 of assigning, to any lattice point of the sheared 3D lattice, the obtained S112 EDT value of the scalar field of the determined S106 nearest lattice point on the constructed S104 auxiliary rectilinear 3D lattice.

The method 100 further includes an act S116 of rendering a medical image based on the assigned S114 (and/or obtained S112) EDT values (e.g., of the sheared volume).

optionally, the method 100 further includes an act S118 of outputting the rendered S116 medical image for display.

Figure 2:
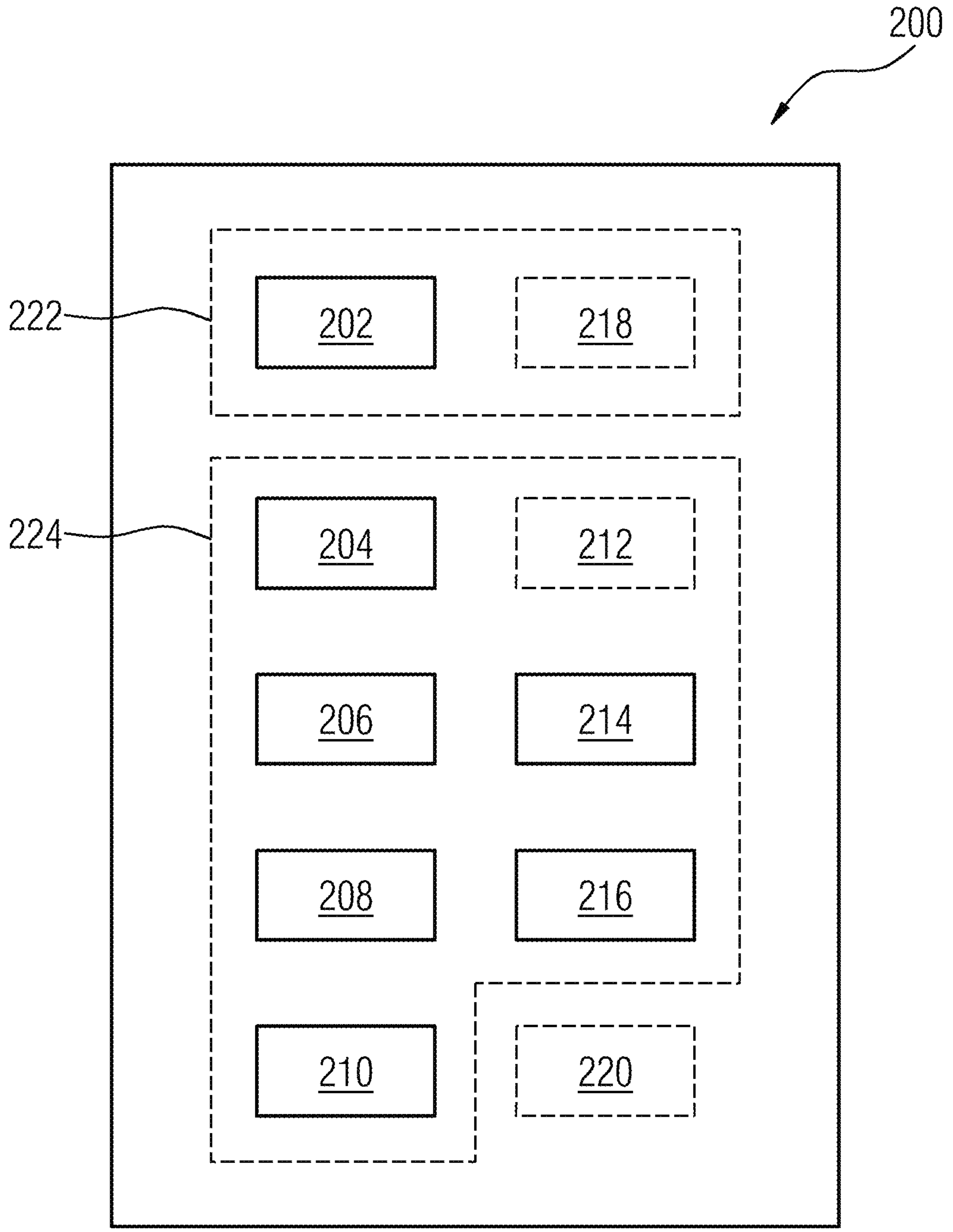
FIG. 2 is an overview of the structure and architecture of a computing device for rendering a medical image associated with a volumetric medical dataset including a sheared volume according to a preferred embodiment, wherein the computing device may be configured to perform the method of FIG. 1.

FIG. 2 schematically illustrates an example of a computing device for rendering a medical image associated with a volumetric medical dataset including a sheared volume. The computing device is generally referred to by reference sign 200.

The computing device 200 includes a volumetric medical dataset receiving interface 202 configured for receiving a volumetric medical dataset from a medical scanner. The medical scanner provides the volumetric medical dataset according to a sheared volume. The sheared volume is represented by a sheared 3D lattice including a series of parallel rectilinear 2D lattices and a series of parallel sheared 1D lattices. Each sheared 1D lattice is non-orthogonal to a 2D plane spanned by any one of the 2D lattices. Each lattice point of the sheared 3D lattice represents a voxel of the volumetric medical dataset. A value of a (e.g., binary) scalar field is associated with the voxel.

The computing device 200 further includes an auxiliary rectilinear constructing module 204 configured for constructing an auxiliary rectilinear volume represented by an auxiliary rectilinear 3D lattice. The auxiliary rectilinear volume includes the sheared volume of the received volumetric medical dataset. A series of auxiliary rectilinear 2D lattices of the auxiliary rectilinear 3D lattice spans the same series of 2D planes as the series of 2D lattice of the sheared 3D lattice with identical 2D lattice constants of the auxiliary rectilinear 2D lattices and the 2D lattice of the sheared 3D lattice. A series of auxiliary 1D lattices of the auxiliary rectilinear 3D lattice is orthogonal to the 2D planes spanned by the 2D lattices. The lattice constant of the auxiliary 1D lattice is determined as the distance between neighboring 2D planes. Neighboring 2D planes are specified by passing through neighboring lattice points along the sheared 1D lattice.

The computing device 200 further includes a determining module 206 configured for determining, for any lattice point of the sheared 3D lattice, the nearest lattice point on the constructed auxiliary rectilinear 3D lattice, or vice versa. Determining the nearest lattice point may include determining a coordinate distance between the lattice point of the sheared 3D lattice and any lattice point on the constructed auxiliary rectilinear 3D lattice and selecting the lattice point with the minimal coordinate distance, to the lattice point of the sheared 3D lattice, among the lattice points on the constructed auxiliary rectilinear 3D lattice. Alternatively, or in addition, determining the nearest lattice point may include determining a coordinate distance between the lattice point of the constructed auxiliary rectilinear 3D lattice and any lattice point on the sheared 3D lattice and selecting the lattice point with the minimal coordinate distance, to the lattice point of the constructed auxiliary rectilinear 3D lattice, among the lattice points on the sheared 3D lattice.

The computing device 200 further includes a first assigning module 208 configured for assigning, to any lattice point of the sheared 3D lattice, the value of the scalar field of the lattice point of the sheared 3D lattice of the determined nearest lattice point on the constructed auxiliary rectilinear 3D lattice.

The computing device 200 further includes an applying module 210 configured for applying, for any lattice point of the constructed auxiliary rectilinear 3D lattice, an EDT to the value of the scalar field assigned to the lattice point of the constructed auxiliary rectilinear 3D lattice. The applying module 210 may be further configured for obtaining an associated EDT value of the scalar field. Alternatively, or in addition, obtaining the associated EDT value of the scalar field may be configured to be performed by a (e.g., separate) obtaining module 212.

The computing device 200 may further includes a second assigning module 214 configured for assigning, to any lattice point of the sheared 3D lattice, the obtained EDT value of the scalar field of the determined nearest lattice point on the constructed auxiliary rectilinear 3D lattice.

The computing device 200 still further includes a rendering module 216 configured for rendering a medical image based on the assigned (and/or obtained, and/or determined) EDT values (e.g., of the sheared volume).

optionally, the computing device 200 further includes an outputting interface 218 configured for outputting the rendered medical image for display.

Further optionally, the computing device 200 may include a memory 220.

Optionally, the volumetric medical dataset receiving interface 202 and the outputting interface 218 may be included in a common (e.g., input-output) interface 222.

Further optionally, any one of the auxiliary rectilinear constructing module 204, the determining module 206, the first assigning module 208, the applying module 210, the obtaining module 212, the second assigning module 214, and/or the rendering module 216 may be included in or instructions configuring a processor 224 and/or processing unit 224, in particular a central processing unit (CPU) and/or a graphics processing unit (GPU).

The computing device 200 may be configured to perform the method 100.

A system for rendering a medical image associated with a volumetric medical dataset including a sheared volume may include a computing device, e.g., the computing device 200 according to FIG. 2. The system may further include one or more medical scanners configured for providing a volumetric medical dataset to a volumetric medical dataset receiving interface (e.g., the interface 202) of the computing device (e.g., the computing device 200). The system may still further include a display device (briefly also: display) configured for receiving a rendered medical image from a rendering module (e.g., the module 216) of the computing device (e.g., the computing device 200). The display device may be further configured for displaying the received medical image.

By the technique (e.g., embodied by the method 100, the computing device 200, and/or the system), a EDT, (e.g., Euclidean) SDT, and/or (e.g., Euclidean) SDF for a volumetric medical dataset (also denoted as 3D medical image) with a sheared volume (and/or sheared 3D lattice of voxels, also denoted as sheared model matrix), e.g., for gantry tilted CT data, may be determined.

Alternatively, or in addition, the technique may be used to determine (e.g., compute) the SDF for a volumetric medical dataset with a sheared volume. Volumetric medical datasets with sheared volumes, although not as widely used now, still exist in medical scans and/or medical imaging. E.g., some (e.g., CT) gantry tilted scans are still needed for (e.g., CT-) guided biopsy and/or (e.g., CT) guided drainage. In particular, the (e.g., CT) tilted gantry scans can help guide the oblique needle procedures more easily (in particular compared to untilted gantry scans). Alternatively, or in addition, brain (e.g., CT scans) sometimes need to tilt the gantry to reduce the amount of radiation to the eyes.

Figure 3:
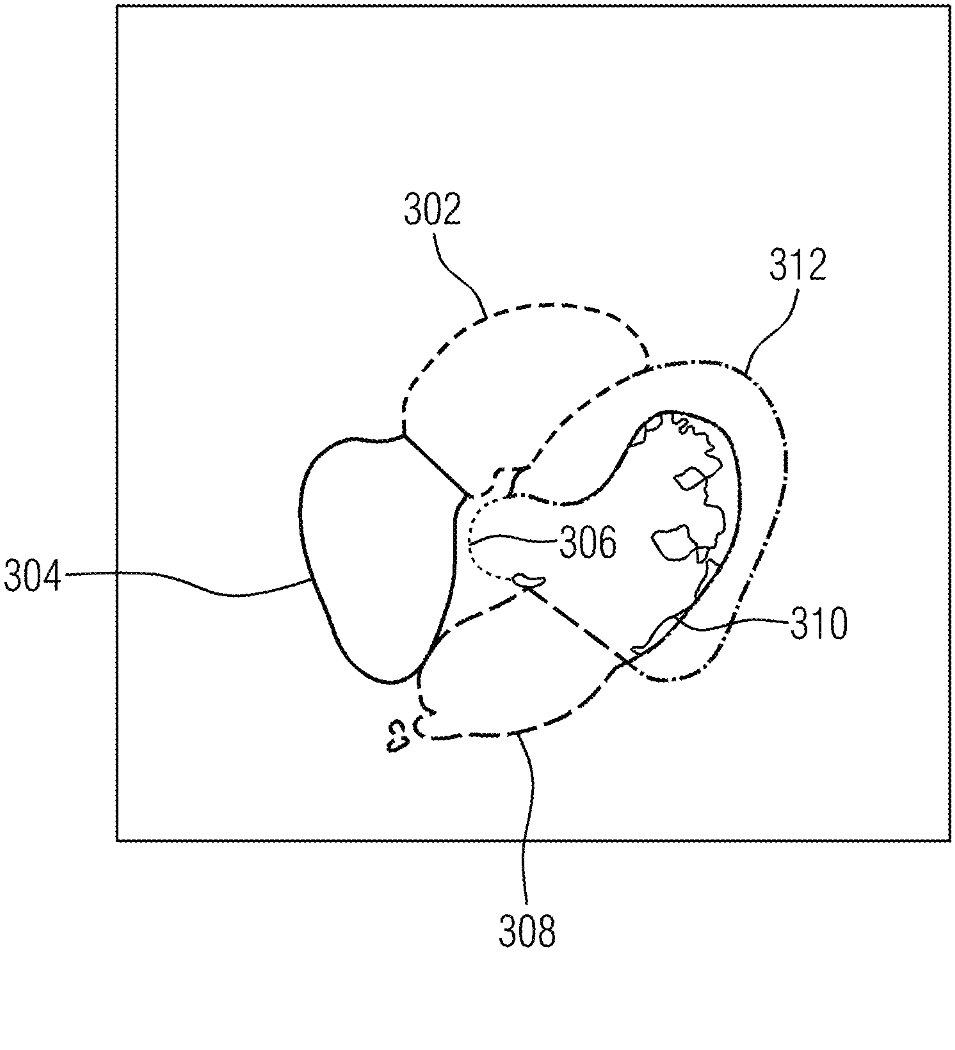
FIG. 3 shows an example of a segmentation of a human heart using a k-ary valued scalar field.

FIG. 3 shows an example of a smooth contour extracted from a k-ary segmentation of a patient's heart. At reference sign 302, a contour (also: boundary) of the right ventricle (RV) is shown. At reference sign 304, the contour (also: boundary) of the right atrium (RA) is shown. At reference sign 306, a contour (also: boundary) of the left ventricle (LV) blood pool is shown. At reference sign 308, a contour (also: boundary) of the left atrium (LA) is shown. At reference sign 310, a contour (also: boundary) of the LV papillary muscles and trabeculations is shown. At reference sign 312, a contour (also: boundary) of the LV myocardium is shown.

The k-ary segmentation of FIG. 3 may be performed as a series of binary segmentations, e.g., in one pass distinguishing background (e.g., not part of the heart) and foreground (e.g., part of the heart), in a second pass distinguishing the RV from any other anatomical structure (in particular including the background), in a third pass distinguishing the LV blood pool from any other anatomical structure in particular including the background), and so forth.

Alternatively, or in addition, to determine (e.g., calculate) the SDF for a scalar value i (with $i=0, 1, \ldots, k-1$) of a k-ary (e.g., scalar) field, the k-ary field may be converted to a binary (e.g., scalar) field (also denoted as Boolean field), in which the voxel of the scalar value i is classified as one (e.g., T, and/or "true") value, and any voxel with a differing scalar value $j \neq i$ is classified as the other (e.g., F, and/or "false") value. The technique may then be applied to the binary field (in particular obtained by the converting), and the SDF for value i can be determined (e.g., calculated).

A Voronoi map may be defined as a function that can return the nearest point in a field with predetermined scalar value (e.g., i with $i=0, 1, \ldots, k-1$) to an input point (e.g., a voxel, and/or pixel). In this sense, the closest point transform (CPT) may correspond to a 3D discrete version of a Voronoi map, where all the points are located on a 3D lattice (e.g., representing voxels, and/or pixels).

Alternatively, or in addition, the SDF may be determined (and/or deducted) from the CPT with point coordinates.

Given a binary n-dimensional image (e.g., with pixel value, and/or voxel value, either T or F), its Euclidean SDF may be defined as an aligned image on the same grid where the absolute value of every pixel, and/or voxel, is the Euclidean distance to the nearest pixel, and/or voxel, of a different value on the binary image, and the sign of the value is positive (or negative) if and only if the binary pixel value is T (or F), or vice versa.

Herein, n may refer to the dimension of the medical dataset, and/or medical image. E.g., n=2 may refer to two-dimensional (2D) medical images, and n=3 may refer to three-dimensional (3D) volumetric medical datasets. Alternatively, or in addition, the (in particular Euclidean) SDF may be determined for any dimension n of the medical image, and/or medical volumetric dataset. In particular, the (e.g., Euclidean) SDF may be determined for 3D datasets, and/or volumetric datasets, received from a medical scanner, e.g., using CT and/or MRI as scanning modality.

The EDT may be defined as taking a scalar field (also denoted as input field) of Booleans (e.g., T and F, and/or "true" and "false", respectively, corresponding to the values of the scalar field) and producing a (e.g., Euclidean distance transformed) field of scalars such that each value in the output is the ED to the nearest "true" pixel, and/or voxel, in the input. It is noted that a ED can be easily determined (e.g., computed) from a squared ED (e.g., by taking the square root) in linear time.

Alternatively, or in addition, the SDF can be determined (e.g., calculated) with two (e.g., independent, and/or separate) EDTs on the T and F values, respectively.

Figure 4C:
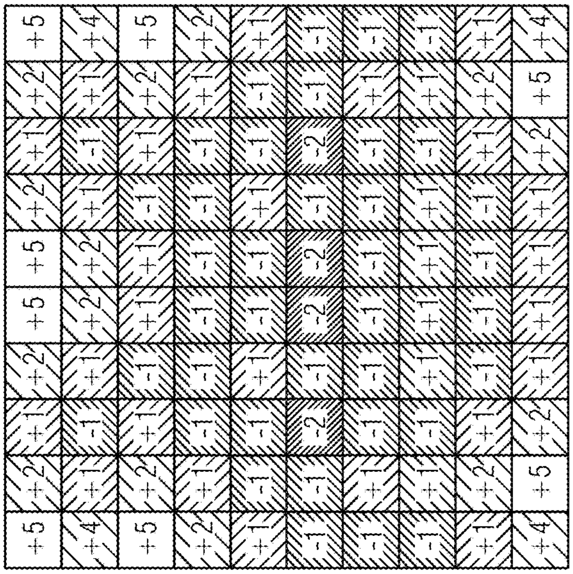
FIG 4C (Prior Art)
FIGS. 4A, 4B and 4C show an example of a two-dimensional (2D) square lattice with binary values (e.g., "T" for true and "F" for false) of a scalar field, the Euclidean distance transform (EDT) for one value of the scalar field, and the signed Euclidean distance transform (SDT) for both values of the scalar field, respectively.
Figure 4B:
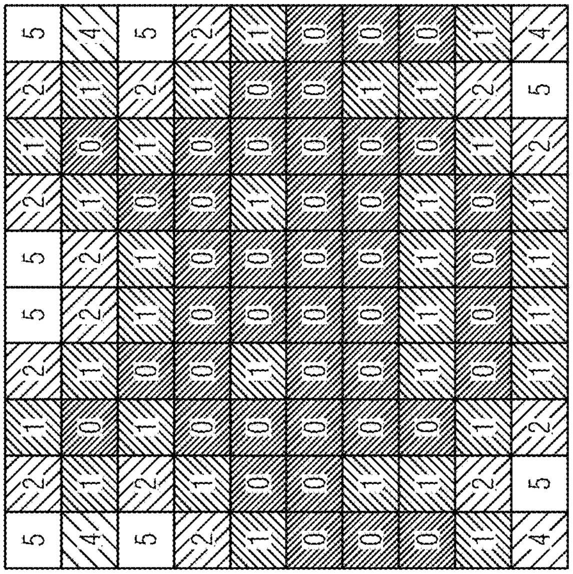
FIG 4B (Prior Art)
Figure 4A:
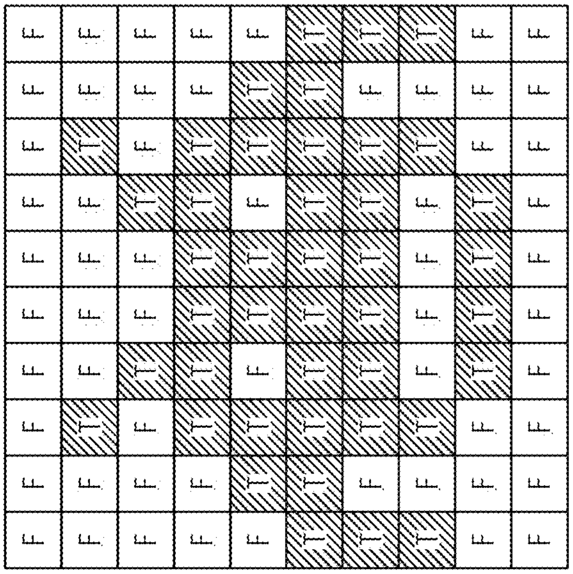
FIG 4A (Prior Art)

FIGS. 4A, 4B and 4C show an example of determining a squared EDT (and/or squared ED), a signed squared EDT (which may also briefly be denoted as squared SDT), and/or a (e.g., squared) SDF. The example of FIGS. 4A, 4B and 4C was previously provided by Philip Rideout and is valid only for square 2D lattices (and/or generalizable to rectilinear 2D lattices, but not sheared 2D lattices).

In FIG. 4A, an input Boolean field with value T or F per pixel of a square lattice (also: grid) is shown. In FIG. 4B, the squared EDT to the nearest pixel having the value T is shown. In FIG. 4C, the SDF, and/or the squared SDT is shown.

The method for determining the squared EDT and the SDF in FIGS. 4B and 4C, respectively, based on the Boolean field of FIG. 4A was previously presented by Pedro F. Felzenszwalb and Daniel P. Huttenlocher, Distance Transforms of Sampled Functions, Theory of Computing, Vol. 8, No. 19, September 2012.

The conventional EDT algorithm, according to Felzenszwalb, for rectilinear grid images (and/or volumes) runs in O (n) time, where n is the total number of pixels (and/or voxels).

Figure 5A:
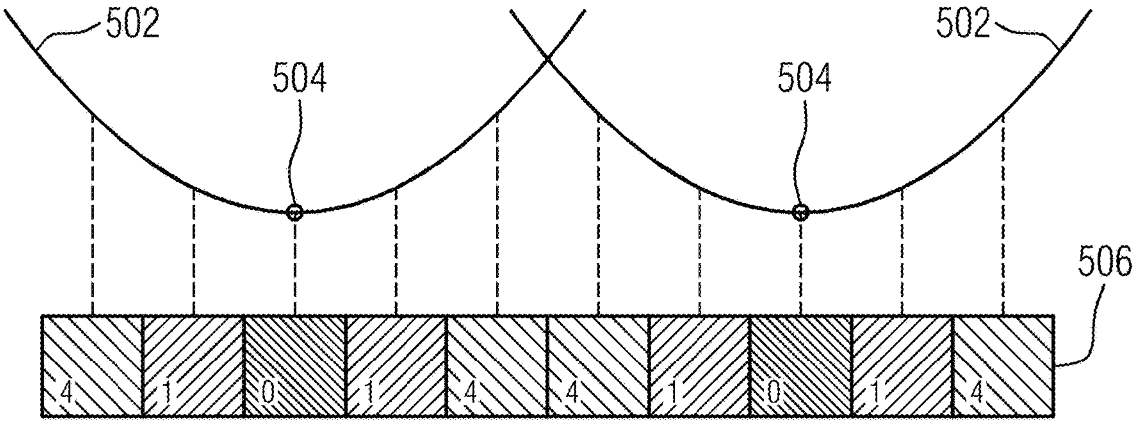
FIG 5A (Prior Art)
FIGS. 5A and 5B show one-dimensional (1D) and 2D examples, respectively, of determining the EDT for one value of a scalar field.

The conventional algorithm of has the following acts:

In a first act, the binary image is converted to a scalar field, where T values are replaced with zero, and F values are replaced with infinity in an initialization act. In a second act, a 1D squarer distance field is determined for every row in the image. The 1D squared distance field is a set of samples from a series of overlapping quadratic parabolas 502, as shown in FIG. 5A. The result of the second act is a scalar field that stores the squared ED to the nearest T value pixels on the same row 506.

In FIG. 5A, which is based on an illustration by Philip Rideout, one row 506 of a squared Euclidean distance field (briefly: distance field), represented by a series of parabolas 502, is shown. 0 represents a pixel of T value. Positive values correspond to the squared EDs to the nearest T value pixel (and/or voxel). One parabola curve 502 is the distance function of one T value pixel (and/or voxel), where the vertex (also denoted as cusp) 504 of the curve 502 is the lowest point on the curve 502 and is located at the T value pixel (and/or voxel). The parabola curves of F value pixels are invisible in FIG. 5A since the corresponding vertex is infinitely away. The squared EDs of other pixels (and/or voxels) within the row 506 are sampled from the lower hull of the parabolas 502, as indicated for each pixel (and/or voxel) by a dashed line.

Figure 5B:
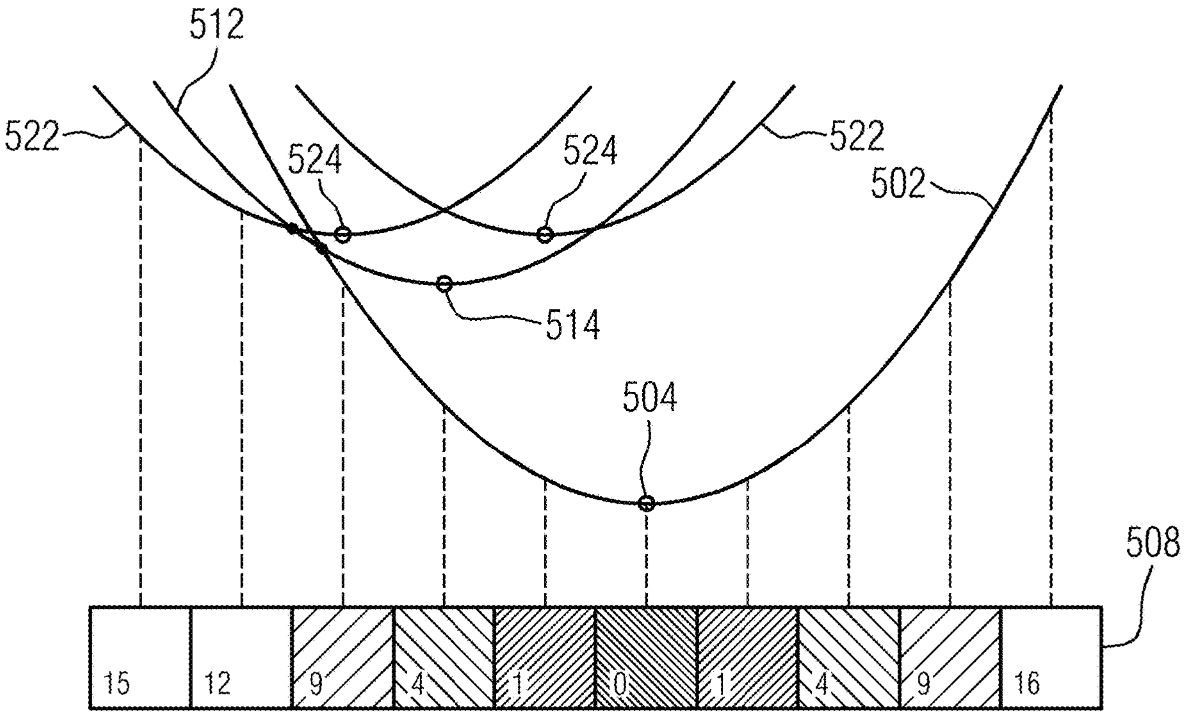
FIG 5B (Prior Art)

In a third act, the 2D squared Euclidean distance field may be determined (e.g., calculated) from the results of the second act. In the third act, the image is processed for every column. As shown in FIG. 5B, for a column 508 of ten (10) pixels (and/or voxels), if the scalar values after the second act is, e.g., [∞, ∞, 9, 4, 1, 0, ∞, ∞, ∞, ∞], the result of the third act should be sampled from the lower hull of the four visible parabolas 502; 512; 522 with vertices 504; 514; 524 at different heights. It is noted that it has to be assumed that the column axis 508 is perpendicular to the row axis 506, for this act to be valid.

In the example, the squared Euclidean distance, e.g., $$d(x_0, y_0) = \min_{x,y}\left((x-x_0)^2 + (y-y_0)^2\right) = \min_{y}\left(\min_{x}\left((x-x_0)^2 + (y-y_0)^2\right)\right),$$

is determined for a 2D image, $$\min_{x}\left((x-x_0)^2 + (y-y_0)^2\right)$$

is evaluated in the second act (e.g., for a first dimension, and/or a row), and the third act evaluates $$\min_{y},$$

e.g., for a second dimension, and/or a column.

FIG. 5B, which is based on another illustration by Philip Rideout, shows a possible row 508 of a distance field after the third act.

For a n×m rectilinear 2D image, all points can be enumerated by $P(i,j) 0 \leq i < n, 0 \leq j < m$. One row (e.g., at reference sign 506 in FIG. 5A) can be defined as a set of points with one same j index, while a column (e.g., at reference sign 508 in FIG. 5B) can be defined as a set of points with the same i index.

In the example of FIG. 5A, the image (and/or volumetric dataset) is processed in rows 506 so that every pixel, and/or voxel, $P_i$ has been assigned with a squared Euclidean distance $D^0(P_i)$ which is the square of the minimum distance from the pixel, and/or voxel, to the nearest T value pixel and/or voxel $C^0(P_i)$ on the same row 506.

In the example of FIG. 5B, the image (and/or volumetric dataset) is processed in columns 508. For one column 508, every pixel, and/or voxel, $P_i$ defines a parabola 502; 512; 522, in which the height of the vertex 504; 514; 524 is the squared Euclidean distance $D^0(P_i)$ (e.g., determined according to the row 506 in FIG. 5A). The squared distance from any pixel, and/or voxel, $P_i$ (on the same column 508 of $P_i$) to $C^0(P_i)=D^0(P_i)$ may be equal, and/or may correspond to $D^0(P_i)+D(P_i, P_j)$, where $D(P_i, P_j)$ is the squared distance from $P_i$ to $P_j$.

Felzenszwalb demonstrated that building and sampling the hull of parabolas 502; 512; 522 is linear in time, since the number of parabolas 502; 512; 522 is no more than the number of pixels (and/or voxels).

The algorithm, e.g., as demonstrated in FIGS. 4A, 4B, 4C, 5A and 5B for a square 2D lattice, can be easily extended to 3D or higher dimensions by repeating the third act at different axes of the image, and/or volume.

Alternatively, or in addition, the original algorithm for a square lattice (also: square grid) may be easily adjusted, and/or generalized, to a rectilinear lattice (also: rectilinear grid) by adjusting the shape (e.g., the width) of the parabolas 502; 512; 522.

The method for determining the EDT, and/or SDF, can also be applied to a closest point transform (CPT), where the resulting field stores the coordinates of the nearest point. Alternatively, or in addition, the closest point coordinates may be easily converted to EDs.

Figure 6:
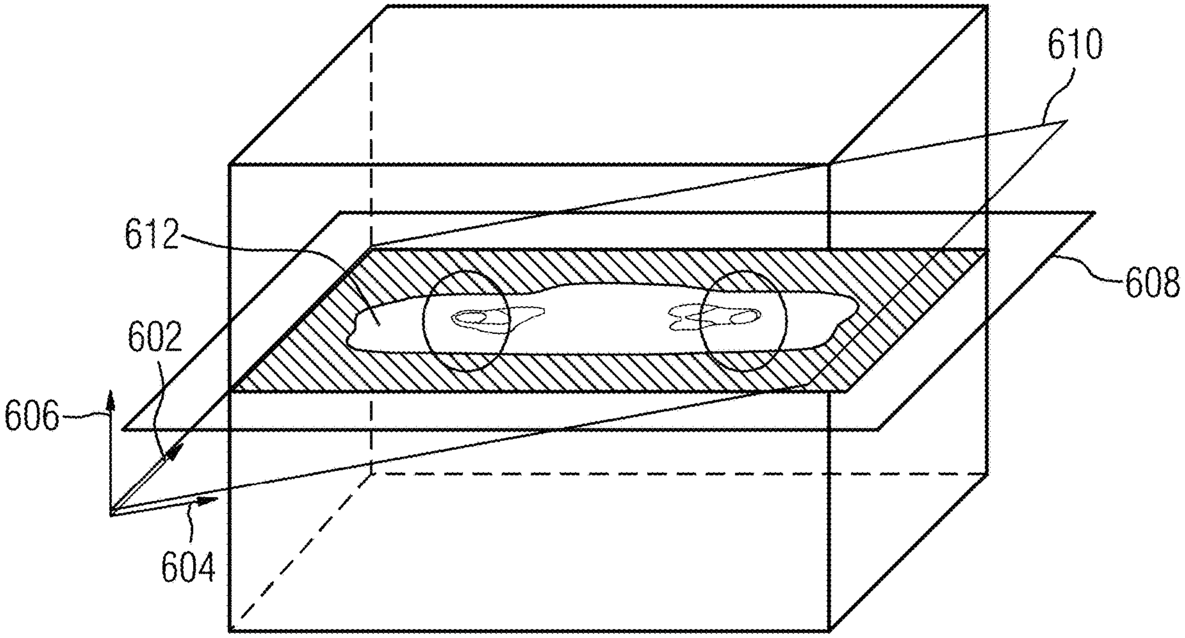
FIG. 6 shows an example of a sheared volume of a volumetric medical dataset arising when performing a medical scan.

FIG. 6 shows an exemplary schematic diagram of a tilted (e.g., CT) scan (e.g., based on an illustration by Changhwan Kim, Rizza Pua, Chung-Hwan Lee, Da-in Choi, Byungchul Cho, Sang-wook Lee, Seungryong Cho, Jungwon Kwak, An additional tilted-scan-based CT metal-artifact-reduction method for radiation therapy planning, Journal of Applied Clinical Medical Physics, Volume 20, Issue 1, pp 237-249).

In FIG. 6, an untilted plane 608 including a human body (and/or at least a part of a human body) 612 is schematically depicted as well as a slice 610, along which the tilted (e.g., CT) scan is performed. The (e.g., at least part of the) human body 612 may be located inside a bounding box, e.g., as indicated by the perspectively depicted shaded rectangular area within the perspectively shown rectangular box. Alternatively, or in addition, the bounding box may refer to the auxiliary rectilinear volume which is constructed to (e.g., tightly) bound the sheared volume of the (e.g., CT) scan.

The coordinate directions at reference signs 602 and 604 may be chosen at right angles. The coordinate directions at reference signs 602 and 604 span a 2D plane, in which the slice 610 lies. The coordinate direction 606 corresponds to the tilted direction defined by the geometry of the gantry used for the (e.g., CT) scan.

A (e.g., 3D) volume V may be specified by a model matrix $M=[\vec{x}, \vec{y}, \vec{z}, \vec{w}]$, where $\vec{x}, \vec{y}, \vec{z}, \vec{w}$ are three-component column vectors, which transform a voxel from its model space to the 3D world space. $\vec{x}, \vec{y}, \vec{z}$ are the three (e.g., coordinate) axes of the volume, and $\vec{w}$ is the origin (e.g., of the coordinate, and/or model, space). The origin may, e.g., be located at a corner of the, e.g., 3D) volume V.

For a rectilinear volume, all three (e.g., coordinate) axes $\vec{x}, \vec{y}, \vec{z}$ are mutually orthogonal, and/or perpendicular to each other. The conventional algorithm of Felzenszwalb relies on the assumption of a rectilinear volume.

For a sheared volume, e.g., of a gantry-tilted (in particular CT) scan (also denoted as image), the two (e.g., coordinate) axes $\vec{x}$ and $\vec{y}$, are perpendicular to each other (and/or mutually orthogonal), but the third (e.g., coordinate) axis $\vec{z}$ is not perpendicular to $\vec{x}$ and $\vec{y}$.

By the technique, the SDF for a sheared volume may be determined (e.g., computed), in particular based on a transformation from the sheared volume to a (e.g., tightly bounding) auxiliary rectilinear volume.

In the following Table 1, the coordinates, vectors of unit length, lattice constants as well as lattice vectors (also denoted as axes) spanning a sheared 3D lattice and a (e.g., tightly bounding) auxiliary rectilinear 3D lattice are listed. Lattice points may be labeled by a triple of integers (i,j,k) and (i', j', k') along the lattice vectors of the sheared and the auxiliary rectilinear (e.g., 3D) volume, respectively.

TABLE 1

Geometric transformations among lattices and/or coordinate systems

| Sheared volume | | | | Auxiliary rectilinear volume | | |
|---|---|---|---|---|---|---|
| x | y | z | Coord. (scalars) | x' | y' | z' |
| $\vec{e}_x =: \hat{x}$ | $\vec{e}_y =: \hat{y}$ | $\vec{e}_z =: \hat{z}$ | Unit vectors | $\vec{e}_{x'} = \vec{e}_x = \hat{x} = \hat{x}'$ | $\vec{e}_{y'} = \vec{e}_y == \hat{y} = \hat{y}'$ | $\vec{e}_{z'} = \vec{e}_x \times \vec{e}_y = \hat{z}' = \hat{x} \times \hat{y}$ |
| $l_x$ | $l_y$ | $l_z$ | Lattice const. (scalars) | $l_x$ | $l_y$ | $l_{z'} = l_z \vec{e}_z \cdot (\vec{e}_x \times \vec{e}_y)$ |
| $\vec{l}_x = l_x \vec{e}_x =: \vec{x}$ | $\vec{l}_y = l_y \vec{e}_y =: \vec{y}$ | $\vec{l}_z = l_z \vec{e}_z = \vec{l}_{z'} + (\vec{e}_{x'} \cdot \vec{l}_z)\vec{e}_x + (\vec{e}_y \cdot \vec{l}_z)\vec{e}_y =: \vec{z}$ | Vectors to neighb. lattice points | $\vec{l}_{x'} = l_{x'} \vec{e}_{x'} =: \vec{x}' = \vec{l}_x = \vec{x}$ | $\vec{l}_{y'} = l_{y'} \vec{e}_{y'} =: \vec{y}' = \vec{l}_y = \vec{y}$ | $\vec{l}_{z'} = l_{z'} \vec{e}_{z'} = l_z [\vec{e}_z \cdot (\vec{e}_x \times \vec{e}_y)]$ <br> $\vec{e}_x \times \vec{e}_y = \vec{l}_z - (\vec{e}_x \cdot \vec{l}_z)\vec{e}_x - (\vec{e}_y \cdot \vec{l}_z)\vec{e}_y = l_z [\vec{e}_z - (\vec{e}_x \cdot \vec{e}_z)\vec{e}_x - (\vec{e}_y \cdot \vec{e}_z)\vec{e}_y] =: \vec{z}' = (\vec{z} \cdot \hat{z}')\, \hat{z}'$ |
| $i\vec{l}_x + j\vec{l}_y + k\vec{l}_z$ with $0 \le i < N_x$, $0 \le j < N_y$, $0 \le k < N_z$ | | | Any lattice points | $i'\vec{l}_{x'} + j'\vec{l}_{y'} + k'\vec{l}_{z'}$ with $0 \le i' < N_{x'}$, $0 \le j' < N_{y'}$, $0 \le k' < N_{z'} = N_z$, with $N_x < N_{x'}$ and/or $N_y < N_{y'}$ | | |

For the boundary slice with k = k' = 0, the 2D lattice points are identical: i = i'; j = j'.

For any non-boundary slice with k = k' > 0, the 2D lattice points are relatively displaced by non-integer fractions (denoted as floating-point numbers) of the lattice constants:

$$i'\vec{l}_{x'} + j'\vec{l}_{y'} + k'\vec{l}_{z'} = i'\vec{l}_x + j'\vec{l}_y + k'\left[\vec{l}_z - \left(\vec{e}_x \cdot \vec{l}_z\right)\vec{e}_x - \left(\vec{e}_y \cdot \vec{l}_z\right)\vec{e}_y\right] =$$

$$\left[i' - k'\frac{l_z}{l_x}\left(\vec{e}_x \cdot \vec{e}_z\right)\right]\vec{l}_x + \left[j' - k'\frac{l_z}{l_y}\left(\vec{e}_y \cdot \vec{e}_z\right)\right]\vec{l}_y + k'\vec{l}_z =: i*\vec{l}_x + j*\vec{l}_y + k*\vec{l}_z$$

Determine a set of the four closest points, to the point (i', j') in the auxiliary rectilinear 2D lattice, in the original 2D lattice of the sheared volume within the same slice k = k' > 0 by taking $(\lfloor i^* \rfloor, \lfloor j^* \rfloor)$ as well as $(\lfloor i^* \rfloor + 1, \lfloor j^* \rfloor)$, $(\lfloor i^* \rfloor, \lfloor j^* \rfloor + 1)$, $(\lfloor i^* \rfloor + 1, \lfloor j^* \rfloor + 1)$. This gives the closest points if both i* and j* are non-integer. If any one of the two is non-integer, the corresponding "+1" will not provide a box, in which the point lies, as the point is already at an edge (or even corner).

Herein, [t] denotes the largest integer smaller or equal to t.

The nearest lattice point within the set of the four closest points may be determined by having the minimal difference between the points (as 2D vectors) within the same slice k = k' > 0, which corresponds to the minimal length within the set of 2D difference vectors given by $(i^* - \lfloor i^* \rfloor, j^* - \lfloor j^* \rfloor)$ as well as $(i^* - \lfloor i^* \rfloor - 1, j^* - \lfloor j^* \rfloor)$, $(i^* - \lfloor i^* \rfloor, j^* - \lfloor j^* \rfloor - 1)$, $(i^* - \lfloor i^* \rfloor - 1, j^* - \lfloor j^* \rfloor - 1)$, respectively.

Inverse transformation for any non-boundary slice with k = k' > 0:

$$i\vec{l}_x + j\vec{l}_y + k\vec{l}_z = i\vec{l}_x + j\vec{l}_y + k\left[\vec{l}_{z'} + \left(\vec{e}_x \cdot \vec{l}_z\right)\vec{e}_x + \left(\vec{e}_y \cdot \vec{l}_z\right)\vec{e}_y\right] =$$

$$\left[i + k\frac{l_z}{l_x}\left(\vec{e}_x \cdot \vec{e}_z\right)\right]\vec{l}_x + + \left[j + k\frac{l_z}{l_y}\left(\vec{e}_y \cdot \vec{e}_z\right)\right]\vec{l}_y + k'\vec{l}_{z'} =: i^+\vec{l}_x + j^+\vec{l}_y + k^+\vec{l}_{z'}$$

Determine a set of the four closest points, to the point (i, j) in the original 2D lattice of the sheared volume, in the auxiliary rectilinear 2D lattice within the same slice by k = k' > 0 taking $(\lfloor i^+ \rfloor, \lfloor j^+ \rfloor)$ as well as $(\lfloor i^+ \rfloor + 1, \lfloor j^+ \rfloor)$, $(\lfloor i^+ \rfloor, \lfloor j^+ \rfloor + 1)$, $(\lfloor i^+ \rfloor + 1, \lfloor j^+ \rfloor + 1)$.

The nearest lattice point within the set of the four closest points may be determined by having the minimal difference between the points (as 2D vectors) within the same slice k = k' > 0, which corresponds to the minimal length within the set of 2D difference vectors given by $(i^+ - \lfloor i^+ \rfloor, j^+ - \lfloor j^+ \rfloor)$ as well as $(i^+ - \lfloor i^+ \rfloor - 1, j^+ - \lfloor j^+ \rfloor)$, $(i^+ - \lfloor i^+ \rfloor, j^+ - \lfloor j^+ \rfloor - 1)$, $(i^+ - \lfloor i^+ \rfloor - 1, j^+ - \lfloor j^+ \rfloor - 1)$, respectively.

Compute distance (= length of each 2D difference vector) in the usual trigonometric way (remember that any one of the, sheared and/or auxiliary rectilinear, 2D lattices is rectilinear).

Determine the nearest point by the minimal distance among the set of four closest points.

In the table above, by using the auxiliary floating point (and/or non-integer) numbers $(i^*,j^*)$ and $(i^+,j^+)$, the nearest point on one lattice (e.g., the constructed auxiliary rectilinear 2D lattice) may be determined for a lattice point on the other lattice (e.g., the original rectilinear 2D lattice of the sheared volume).

Figure 7A:
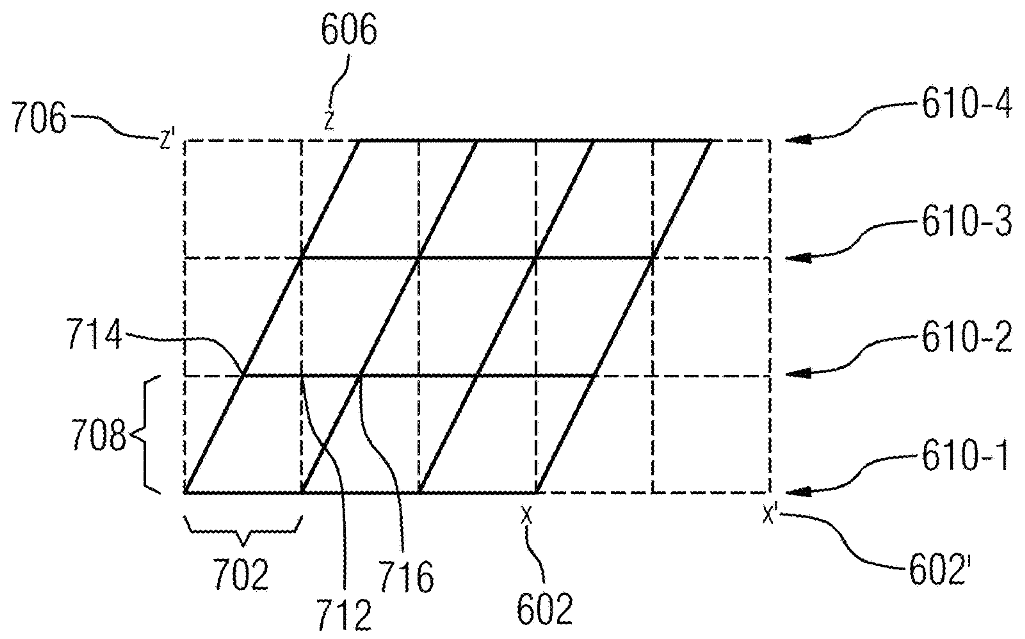
FIGS. 7A and 7B exemplarily illustrate the construction of an auxiliary rectilinear three-dimensional (3D) lattice including the sheared volume, e.g., received by the medical scan of FIG. 6, with a shared 3D lattice representing the voxels of the volumetric medical dataset, and further exemplarily illustrate determining the nearest lattice point on the corresponding rectilinear 2D lattices.
Figure 7B:
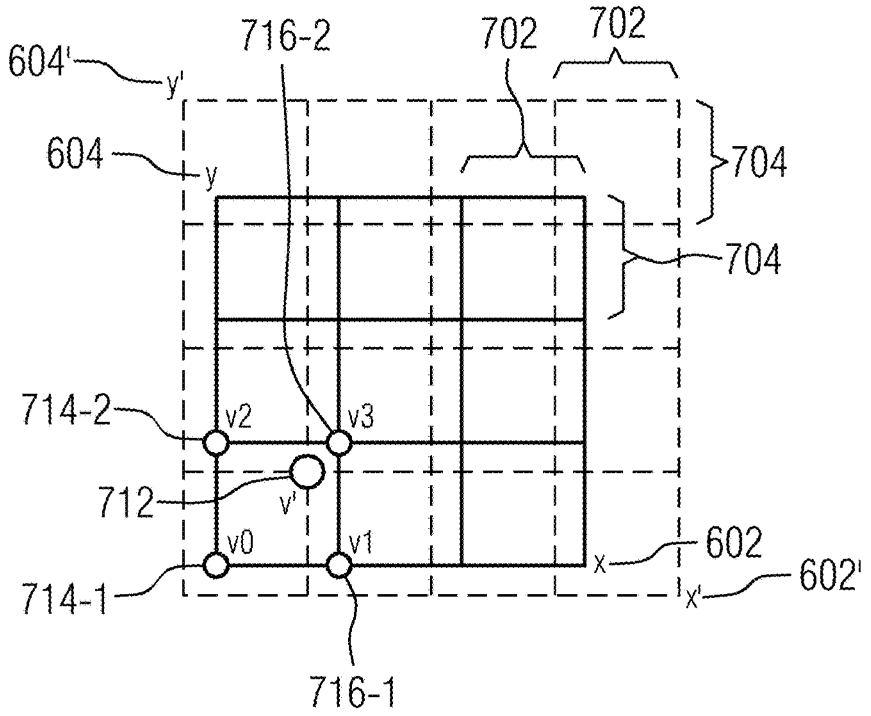

According to an embodiment of the technique, the following acts may be performed, as schematically illustrated in FIGS. 7A and 7B.

In a first act, a (e.g., auxiliary) rectilinear volume V' may be constructed (e.g., according to the act S104 of the method 100) that tightly bounds the input (e.g., received according to the act S104 of the method 100) sheared volume V. The x' axis 602' and y' axis 604' of the auxiliary volume V' are the same as the x axis 602 and the y axis 604 of the sheared volume V, respectively, except for a relative displacement of the origin, in particular depending on the corresponding slice 610-1; 610-2; 610-3; 610-4 (e.g., for the boundary slice 610-1 in FIG. 7A, no displacement occurs, while the displacement increases with every consecutive slice 610-2; 610-3; 610-4 in FIG. 7A, e.g., the points 714 and 716 are lattice points on the sheared lattice in the first displaced slice 610-2, whereas the point 712 is a lattice point in the auxiliary rectilinear lattice). The z' axis 706 of V' is (e.g., except for the length scale) the cross product of the vectors associated with the axes x' and y' at reference signs 602' and 604', respectively, to guarantee that the auxiliary volume V' is rectilinear. Note that the voxel size and/or distance on the auxiliary volume V' may be adjusted so that every z slice 610-1; 610-2; 610-3; 610-4 of the sheared volume V is located on a z' slice 610-1; 610-2; 610-3; 610-4 of the auxiliary volume V'.

FIG. 7A schematically illustrates an auxiliary rectilinear volume V' (with the corresponding rectilinear lattice indicated by dashed lines and x' and z' axes at reference signs 602' and 706, respectively) that tightly bounds the sheared volume V (with the corresponding sheared lattice indicated by solid lines and x and z axes at reference signs 602 and 606, respectively).

As the example of FIG. 7A illustrates, the auxiliary rectilinear lattice with six ($N_{x'}$=6) lattice points per slice 610-1; 610-2; 610-3; 610-4 tightly bounds the sheared lattice with four ($N_x$=4) lattice points per slice 610-1; 610-2; 610-3; 610-4. Said differently, the auxiliary rectilinear volume V' tightly bounding the sheared volume V denotes that no smaller rectilinear volume with identical slices and identical distance among the slices exists. As further illustrated in FIG. 7A, the lattice constant 702, which corresponds to the spacing of the lattice points along the associated direction, is identical along the x direction 602 and the x' direction 602'. As schematically illustrated in FIG. 7B, also the lattice constant 704 along the y direction 604 and the γ' direction 604' is identical. By contrast, as schematically illustrated in FIG. 7A, the lattice constants along the z direction 606 and the z' direction 706 differ but are related by the lattice constant 708 of the auxiliary rectilinear lattice along the z' direction corresponding to the distance among neighboring slices 610-1; 610-2; 610-3; 610-4 of the sheared lattice (and/or sheared volume).

In a second act, for every slice 610-1; 610-2; 610-3; 610-4 of the sheared volume V, a CPT algorithm is used to determine (e.g., calculate) the closest point coordinates on the slices 610-1; 610-2; 610-3; 610-4. Because the x axis 602 and the y axis 604 of V are perpendicular to each other, every slice 610-1; 610-2; 610-3; 610-4 of V corresponds to a rectilinear 2D image. Alternatively, or in addition, the conventional EDT, SDT, and/or SDF algorithms of [1,2] may be applied (and/or is still valid).

FIG. 7B exemplarily illustrates finding the nearest lattice point (e.g., representing a pixel, and/or voxel) on the sheared volume V, e.g., to the point denoted by v' at reference sign 712 on a z' slice (also denoted as z' line) of the auxiliary rectilinear volume V'. As illustrated in FIG. 7B, within the z' slice, the point v' at reference sign 712 is located inside a rectangle of the z slice with (e.g., corner) points v0, v1, v2, and v3 at reference signs 714-1, 716-1, 714-2 and 716-2, respectively, of the sheared volume V.

In a third act, an iteration through every z' slice (and/or z' line) 610-1; 610-2; 610-3; 610-4 (in particular for fixed x' and y' coordinates 602' and 604', respectively) of the auxiliary rectilinear volume V' is performed. In a z' slice (and/or z' line) 610-1; 610-2; 610-3; 610-4, every voxel (and/or pixel) is located in one of the z slices of the sheared volume V. Since the z direction 606 is not perpendicular to the x and y directions 602 and 604, respectively, a voxel (and/or pixel) on the z' slice (and/or z' line) is not an exact voxel in the sheared volume V. Instead, it should be located inside a rectangle of the (e.g., original) 2D lattice. For the vertices of the rectangle, the closest coordinates on the slice have been computed in the second act. E.g., as exemplarily illustrated in FIG. 7B, the pixel v' at reference sign 712 on a z' slice (and/or z' line) is located inside the rectangle [v0, v1, v2, v3] with the vertex points v_i depicted at reference signs 714-1, 716-1, 714-2 and 716-2 for i=0, 1, 2 and 3, respectively. Alternatively, or in addition, supposing that the closest point to v_i on slice z is c_i, then obviously, the closest point on slice z to v' is one of points [c0, c1, c2, c3], which can be easily determined (e.g., calculated) by comparing the distance from c_i (i=0, 1, 2, 3) to v'.

It is noted that every z' slice 610-1; 610-2; 610-3; 610-4 of the auxiliary rectilinear volume lies on one slice (slice z) 610-1; 610-2; 610-3; 610-4 of the sheared volume V, and vice versa.

In a fourth act, the same algorithm (e.g., according to [1,2]) in the third act of the determining of the EDT, SDT, and/or SDF on a rectangular lattice (also: rectangular grid) may applied to the scalar field on the auxiliary rectilinear volume V'. Alternatively, or in addition, the CPT may be determined (e.g., computed) on the auxiliary rectilinear volume (and/or lattice).

In a fifth act, the EDT, SDT, SDF, and/or CPT of the auxiliary rectilinear volume V' may be converted to the EDT, SDT, and/or SDF of the sheared volume V by determining (e.g., calculating) the Euclidean distance from the coordinates.

In the technique according to the above embodiment, the second act and the fourth act are similar to the conventional CPT, EDT, SDT, and/or SDF algorithms, and the time complexity is linear. In the third act and the fifth act, the execution time is also proportional to the number of voxels in the auxiliary rectilinear volume V'. So, the total time for determining the CPT, EDT, SDT, and/or SDF on a sheared volume is still linear.

Figures 8A, 8B, 8C, 8D, 8E, 8F, 8G, 8H:
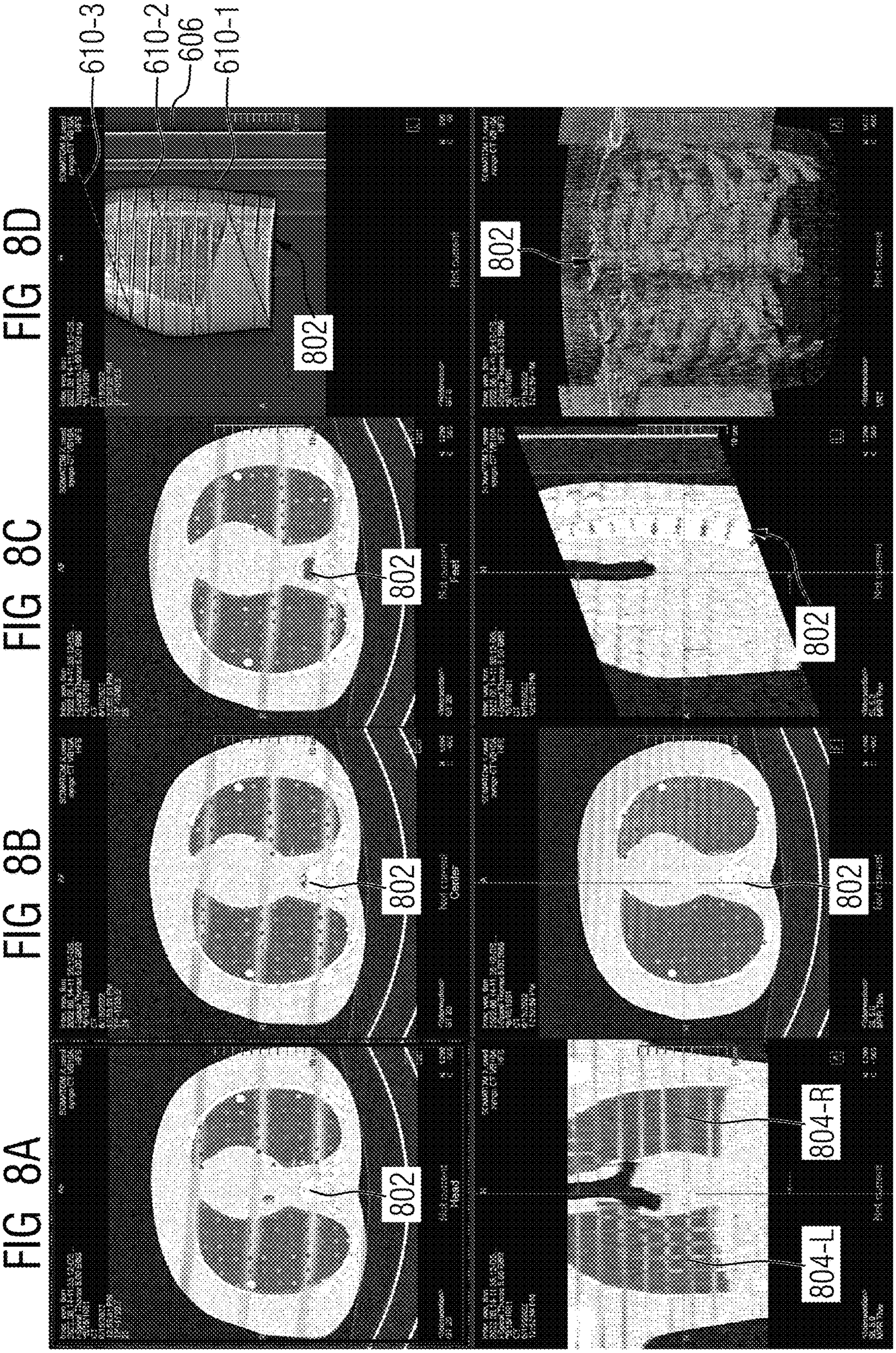
FIGS. 8A to 8H exemplify two-dimensional images based on a tilted CT scan.

FIGS. 8A to 8H show a tilted CT scan, which is created from a phantom dataset for illustrative purposes (e.g., the regular dots approximately arranged in a grid in FIGS. 8A, 8B, 8C, 8F and the roughly horizontal lines in FIGS. 8A, 8B, 8C, 8E, 8F and 8G as well as the horizontal ellipses in FIG. 8D are intrinsic artefacts of the phantom dataset). The phantom dataset in particular illustrates features of real-life CT tilted gantry images for clinical usage.

The three views in FIGS. 8A, 8B and 8C show three 2D axial slices (also denoted as 2D images) in the dataset, which are contiguous 2D slices centered around line 610-2 displayed in FIG. 8D. The dataset contains 47 2D images in total, each 2D image of resolution 512 by 512. The origin of the No. i 2D image is: (−174.658203125,−324.658203125,−1643.459+i*4.8). The orientation of all 2D images is x=(1, 0,0) and y=(0, 0.9396926208, 0.3420201433). The z axis 606 of the sheared volume (in FIG. 8D) is z=(0,0,1), which is not perpendicular to the y axis. The z' axis of the bounding rectilinear volume should be (0,−0.3420201433, 0.9396926208). On each 2D image in FIGS. 8A, 8B and 8C, the pixel spacing (size, and/or lattice constants along x and y direction) is (0.68359375, 0.68359375) in millimeter. The distance between two neighboring 2D images (and/or the lattice constant of the auxiliary z' direction) is 4.8 millimeter.

In any one of FIGS. 8A to 8H, at reference sign 802, the spine is shown. In FIG. 8E, at reference signs 804-L and 804-R, the left and right lobes, respectively, of the lung are indicated. In any of the FIGS. 8A to 8H, "GT" stands for gantry tilted degrees. GT 20 thus denotes a 20-degree tilt of the gantry in FIGS. 8A, 8B and 8C.

In FIG. 8D, a topogram 2D image without a tilt of the gantry (i.e., GT 0) is shown, which is not part of the 3D data used in FIGS. 8A, 8B and 8C, but of a different series scanned previously. The sheared volume with 2D slices 610-1; 610-2; 610-3 outlines the scanned range, which corresponds to the range for the images displayed in FIGS. 8A, 8B, 8C and 8E, 8F, 8G and 8H.

FIG. 8E to 8H show the dataset in 3D (e.g., instead of just 2D slices as in FIGS. 8A, 8B and 8C). FIGS. 8E, 8F, and 8G correspond to the Anterio, Axial, and Sagittal multiplanar reformatted (MPR) views, while FIG. 8H shows a volume rendering of the 3D dataset. In FIGS. 8E, 8F, and 8G, SL 5.0 denotes the thickness of the MPR image (e.g., wherein MPR corresponds to a first 3D rendering method). In FIG. 8G, VRT denotes volume rendering technique (e.g., wherein VRT corresponds to a second 3D rendering method). W and C denote windowing and center of the transfer function used for the corresponding images in FIGS. 8A to 8H.

According to another embodiment of the technique, the scalar value is either T or F (e.g., as binary scalar values), and the three axes of a voxel of the sheared volume V' are denoted as $\vec{x}, \vec{y}, \vec{z}$. The coordinates of a voxel of index (i,j, k) given by $i\vec{x}+j\vec{y}+k\vec{z}$.

The three axes $\vec{x}'$, $\vec{y}'$, $\vec{z}'$ of the voxel in the auxiliary rectilinear volume V' according to the embodiment may be determined (e.g., calculated) from the three axes $\vec{x}, \vec{y}, \vec{z}$ of the (e.g., input) sheared volume V from a medical scanner with the following equations:

$$\begin{cases} \vec{x}' & = \vec{x} \\ \vec{y}' & = \vec{y} \\ \vec{Z}' & = \left(\vec{Z} \cdot \frac{\vec{x} \times \vec{y}}{\|\vec{x} \times \vec{y}\|}\right) \frac{\vec{x} \times \vec{y}}{\|\vec{x} \times \vec{y}\|} \end{cases},$$

wherein · represents the vector dot product (also denoted as scalar product), X represents the vector cross product, $\| \ \|$ represents the length of a vector, and wherein the coordinates of an auxiliary voxel of index (i',j',k') are given by $i'\vec{x}'+j'\vec{y}'+k'\vec{z}'$ (see, e.g., also Table 1 above).

Determining, for any voxel of index (i,j,k) on the 2D lattices (602, 604) for fixed k, the index C (i,j,k) of the closest voxel on the 2D lattice with a different scalar value (e.g., F vs. T), may be performed using the conventional CPT algorithm for rectilinear lattices.

For any lattice point 712 of index (i',j',k') on the constructed auxiliary rectilinear 2D lattice (602', 604'), the index (i*,j*,k*) on the (e.g., input) sheared volume from the medical scanner may be determined (e.g., calculated) with the following equation:

$$\begin{cases} i* & = i' - k'\vec{z} \cdot \frac{\vec{x}}{\|\vec{x}\|} \\ j* & = j' - k'\vec{z} \cdot \frac{\vec{y}}{\|\vec{y}\|} \\ k* & = k' \end{cases},$$

wherein i*,j* are floating point numbers and at least the nearest lattice point 714; 714-1; 714-2; 716; 716-1; 716-2 on the rectilinear 2D lattice (602, 604) within the same 2D plane 610-1; 610-2; 610-3; 610-4 (see, e.g., also Table 1 above).

The indices of the lattice points 714-1, 714-2, 716-1, 716-2 on the (e.g., input) sheared volume are $(i^1,j^1, k^1)=(\lfloor i^* \rfloor, \lfloor j^* \rfloor, k^*)$, $(i^2,j^2, k^2)=(i^1,j^1+1, k^1)$, $(i^3, j^3, k^3)=(i^1+1,j^1, k^1)$, $(i^4, j^4, k^4)=(i^1+1, j^1+1,k^1)$, respectively. Herein, $\lfloor t \rfloor$ represents the integer part of floating point (and/or non-integer) number t.

The lattice points 714-1, 714-2, 716-1 716-2 may be denoted by indices $(i^t, j^t, k^t)$, t=1, 2, 3, 4, and the closest voxels with different scalar values (e.g., F vs. T) on the 2D lattice may be denoted as $C(i^t, j^t, k^t)$, t=1, 2, 3, 4. E.g., there are four voxels (e.g., denoted as set $P_F$) of T scalar value and/or four voxels (e.g, denoted as set $P_F$) of F scalar value. The coordinates of each voxel (in particular on the sheared lattice) are determined easily from its index. The distance from each voxel to the auxiliary rectilinear lattice point (i',j',k') is determined from the coordinates of (i',j',k') and coordinates of each voxel. E.g., the voxel with minimum distance to (i', j',k') in $P_T$ is determined as the closest point with T scalar value (e.g., denoted as $$C_T^1(i', j', k'))$$

to (i',j',k'), e.g., at reference sign 712 in FIGS. 7A and 7B on the auxiliary rectilinear 2D lattice (602', 604'). Alternatively, or in addition, the voxel with minimum distance to (i',j',k') in Pp is determined as the closest point with F scalar value (e.g., denoted as $$C_F^1(i', j', k'))$$

to (i', j',k'), e.g., at reference sign 712 in FIGS. 7A and 7B on the auxiliary rectilinear 2D lattice (602', 604').

The conventional CPT algorithm may be applied to determine the closest point to every auxiliary lattice point P'=(i',j', k') (e.g., at reference sign 712 in FIGS. 7A and 7B) on the auxiliary rectilinear 3D volume with F scalar value. The procedure can be abstracted with the following acts, in which the dimension of the auxiliary rectilinear volume is denoted as $(N_{x'}, N_{y'}, N_{z'})$, and an iteration through all auxiliary lattice points includes $N_{x'} N_{y'}$ instances per slice and $N_{z'}$ slices:

for i' := 0 to $N_{x'} - 1$ {
  for j' := 0 to $N_{y'} - 1$ {
    $C_F^2(i', j', 0) := C_F^1(i', j', 0);$
    for k' := 1 to $N_{z'} - 1$ {
      $P_1 := C_F^2(i', j', k' - 1); P_2 := C_F^1(i', j', k');$
      $$C_F^2(i', j', k') := \begin{cases} P_1, D(P_1, P') < D(P_2, P') \\ P_2, D(P_1, P') \geq D(P_2, P') \end{cases}$$
    }
    $C_F^3(i', j', N_z - 1) := C_F^2(i', j', N_z - 1);$
    for k' := $N_z - 2$ to 0 {
      $P_1 := C_F^3(i', j', k' + 1); P_2 := C_F^2(i', j', k');$
      $$C_F^3(i', j', k') := \begin{cases} P_1, D(P_1, P') < D(P_2, P') \\ P_2, D(P_1, P') \geq D(P_2, P') \end{cases}$$
    }
  }
}

In the abstracted procedure, $$C_F^2(i', j', k')$$

denotes the index of the closest point with F scalar value to auxiliary lattice point P'=(i', j',k') on the slices 0 to k' of the auxiliary rectilinear volume, wherein $$C_F^3(i', j', k')$$

is the index of the closest point with F scalar value to P'=(i',j',k') on all slices of the auxiliary rectilinear volume.

From lines L3 to L7, scanning one line of auxiliary points in ascending third index order (k'=0, 1, 2, . . . ) is performed. When scanning P'=(i',j',k'), the closest point is either $$C_F^2(i', j', k' - 1),$$

which is the closest point (i',j',k'−1) in slices 0 to k'−1 or $$C_F^1(i', j', k'),$$

which is the closest point to (i',j', k') on slice k', whichever is closer to P', wherein D ($P_1$, P') represents the distance from $$P_1 = C_F^2(i', j', k' - 1)$$

to P'=(i', j', k') that is determined from the coordinates of the points.

From lines L8 to L12, scanning the line of points in descending third index order (k'=$N_z$−1, $N_z$−2, $N_z$−3, . . . ) is performed to determine $$C_F^3(i', j', k')$$

with $$C_F^3(i', j', k' + 1)$$

and $$C_F^2(i', j', k').$$

The similar procedure can be applied to determine the closest point $$C_T^3(i', j', k')$$

to (i',j',k') (e.g., at reference sign 712 in FIGS. 7A and 7B) on the auxiliary rectilinear 3D volume with T scalar value.

For any lattice point (i,j,k) on the (e.g., input) sheared volume, the index ($i^+$,$j^+$,$k^+$) on the auxiliary rectilinear volume may be determined with the equation:

$$\begin{cases} i^+ & = i + k\vec{z} \cdot \frac{\vec{x}}{\|\vec{x}\|} \\ j^+ & = j + k\vec{z} \cdot \frac{\vec{y}}{\|\vec{y}\|} \\ k^+ & = k \end{cases},$$

wherein $i^+$, $j^+$ are floating point numbers (and/or non-integers) and the indices of the four nearest auxiliary lattice points are ($i^5$,$j^5$, $k^5$)=($\lfloor i^+ \rfloor$, $\lfloor j^+ \rfloor$, $k^+$), ($i^6$, $j^6$, $k^6$)=($i^5$, $j^5$+1, $k^5$), ($i^7$, $j^7$, $k^7$)=($i^5$+1, $j^5$, $k^5$), ($i^8$,$j^8$, $k^8$)=($i^5$+1, $j^5$+1, $k^5$) respectively. If the (e.g., sheared, and/or original) lattice point (i,j,k) has T scalar value, the minimum distance d to the point (i,j,k) may be determined from the four points $$\{C_F^3(i^5, j^5, k^5), C_F^3(i^6, j^6, k^6), C_F^3(i^7, j^7, k^7), C_F^3(i^8, j^8, k^8)\}$$

with the point coordinates, and the negative value-d may be assigned as the signed Euclidean distance from (i,j,k) to the closest point of F scalar value in the (e.g., input) sheared volume. If the (e.g., sheared, and/or original) lattice point (i,j,k) has F scalar value, the minimum distance d to (i,j,k) may be determined from the four points $$\{C_T^3(i^5, j^5, k^5), C_T^3(i^6, j^6, k^6), C_T^3(i^7, j^7, k^7), C_T^3(i^8, j^8, k^8)\}$$

with the point coordinates, and the positive value d may be assigned as the signed Euclidean distance from (i,j,k) to the closest point of T scalar value in the input volume (and/or the sheared volume).

A method for rendering a medical image associated with a volumetric medical dataset, which is received from a medical scanner, including a sheared volume is provided by the technique. The sheared volume includes a series of 2D slices and a sheared direction. An auxiliary rectilinear volume is constructed such that the 2D slices are preserved, albeit with displaced 2D lattice, and the sheard direction is replaced by a direction orthogonal to the 2D slices. Nearest points on the sheared and the auxiliary rectilinear 3D lattices are determined. A value of a (e.g., binary) scalar field at a point on the sheared 3D lattice is assigned to the nearest point on the auxiliary rectilinear 3D lattice, where a Euclidean distance transform (EDT) is applied to the value of the scalar field. Based on the EDT value of the scalar field, the medical image is rendered.

The technique can be used to compute the SDF for gantry tiled volume and other sheared medical images efficiently, and/or for real-time applications. The technique can be easily extended to higher dimensional data. The obtained SDF can be used, e.g., to accelerate ray tracing based volume rendering for empty space skipping, smooth contour and/or mesh extraction from binary volumes.

Wherever not already described explicitly, individual embodiments, or their individual aspects and features, described in relation to the drawings can be combined or exchanged with one another without limiting or widening the scope of the described invention, whenever such a combination or exchange is meaningful and in the sense of this invention. Advantages which are described with respect to a particular embodiment of present invention or with respect to a particular figure are, wherever applicable, also advantages of other embodiments of the present invention.

The invention claimed is:

1. A computer-implemented method for rendering a medical image associated with a volumetric medical dataset comprising a sheared volume, the method comprising:

receiving the volumetric medical dataset from a medical scanner, wherein the medical scanner provides the volumetric medical dataset according to the sheared volume, wherein the sheared volume is represented by a sheared three-dimensional (3D) lattice comprising a series of parallel rectilinear two-dimensional (2D) lattices and a series of parallel sheared one-dimensional (1D) lattices, wherein each sheared 1D lattice is non-orthogonal to a 2D plane spanned by any one of the 2D lattices, and wherein each lattice point of the sheared 3D lattice represents a voxel of the volumetric medical dataset, wherein a value of a scalar field is associated with the voxel;

constructing an auxiliary rectilinear volume represented by an auxiliary rectilinear 3D lattice, wherein the auxiliary rectilinear volume comprises the sheared volume of the received volumetric medical dataset, wherein a series of auxiliary rectilinear 2D lattices of the auxiliary rectilinear 3D lattice spans the same series of 2D planes as the series of 2D lattice of the sheared 3D lattice with identical 2D lattice constants of the auxiliary rectilinear 2D lattices and the 2D lattice of the sheared 3D lattice, and wherein a series of auxiliary 1D lattices of the auxiliary rectilinear 3D lattice is orthogonal to the 2D planes spanned by the 2D lattices, and wherein a lattice constant of the auxiliary 1D lattice is determined as the distance between neighboring 2D planes, wherein the neighboring 2D planes are specified by passing through neighboring lattice points along the sheared 1D lattice;

determining, for any of the lattice points of the sheared 3D lattice, a nearest lattice point on the constructed auxiliary rectilinear 3D lattice, wherein determining the nearest lattice point comprises determining a coordinate distance between the lattice point of the sheared 3D lattice and any lattice point on the constructed auxiliary rectilinear 3D lattice and selecting the lattice point with the minimal coordinate distance to the lattice point of the sheared 3D lattice, among the lattice points on the constructed auxiliary rectilinear 3D lattice;

assigning, for any of the lattice points of the sheared 3D lattice, the value of the scalar field of the lattice point of the sheared 3D lattice to the determined nearest lattice point on the constructed auxiliary rectilinear 3D lattice;

applying, for any of the lattice points of the constructed auxiliary rectilinear 3D lattice, a Euclidean distance transform (EDT) to the value of the scalar field assigned to the lattice point of the constructed auxiliary rectilinear 3D lattice and obtaining an associated EDT value of the scalar field;

assigning, to any of the lattice points of the sheared 3D lattice, the obtained associated EDT value of the scalar field of the determined nearest lattice point on the constructed auxiliary rectilinear 3D lattice; and rendering a medical image based on the assigned EDT values of the sheared volume.

2. The method according to claim 1, wherein determining, for any of the lattice points of the sheared 3D lattice, the nearest lattice point on the constructed auxiliary rectilinear 3D lattice comprises applying a Voronoi map.

3. The method according to claim 1, wherein the series of rectilinear 2D lattices comprises a series of square 2D lattices.

4. The method according to claim 1, wherein the scalar field associated with the voxel comprises a binary field and/or a k-ary field with k being a natural number greater than, or equal to, two.

5. The method according to claim 1, wherein applying the EDT to the value of the scalar field associated with the voxel represented by the lattice point comprises applying a signed EDT (SDT) wherein the sign of the SDT value of the scalar field at the voxel is based on the value of the scalar field at the voxel in the received volumetric medical dataset.

6. The method according to claim 1, wherein applying the EDT to the value of the scalar field associated with the voxel represented by the lattice point comprises a closest point transform (CPT).

7. The method according to claim 1, wherein the value of the scalar field associated with the voxel of the received volumetric medical dataset is indicative of an anatomical structure.

8. The method according to claim 1, wherein the rendered medical image comprises:

a contour of an anatomical structure;

a segmentation of an anatomical structure; or a volume representation of an anatomical structure.

9. The method according to claim 1, wherein rendering the medical image comprises performing a ray tracing algorithm.

10. The method according to claim 9, wherein the ray tracing algorithm uses, based on the Euclidean distance transformed scalar field, empty space skipping.

11. The method according to claim 1, further comprising:

outputting the rendered medical image for display.

12. The method according to claim 1, wherein the medical scanner includes:

a computed tomography scanner;

a magnetic resonance imaging scanner;

an ultrasound scanner;

a positron emission tomography scanner; or a single-photon emission tomography scanner.

13. The method according to claim 1, wherein the medical scanner comprises a gantry, and wherein the received volumetric medical dataset comprises the sheared volume according to an oblique position of the gantry relative to a patient table.

14. The method according to claim 1, wherein the medical image is used for optical guidance by the medical scanner during an oblique needle procedure.

15. A system for rendering a medical image associated with a volumetric medical dataset comprising a sheared volume, the system comprising:

an interface configured for receiving the volumetric medical dataset from a medical scanner, wherein the medical scanner provides the volumetric medical dataset according to the sheared volume, wherein the sheared volume is represented by a sheared three-dimensional (3D) lattice comprising a series of parallel rectilinear two-dimensional (2D) lattices and a series of parallel sheared one-dimensional (1D) lattices, wherein each sheared 1D lattice is non-orthogonal to a 2D plane spanned by any one of the 2D lattices, and wherein each lattice point of the sheared 3D lattice represents a voxel of the volumetric medical dataset, wherein a value of a scalar field is associated with the voxel;

a processor configured to:

construct an auxiliary rectilinear volume represented by an auxiliary rectilinear 3D lattice, wherein the auxiliary rectilinear volume comprises the sheared volume of the received volumetric medical dataset, wherein a series of auxiliary rectilinear 2D lattices of the auxiliary rectilinear 3D lattice spans the same series of 2D planes as the series of 2D lattice of the sheared 3D lattice with identical 2D lattice constants of the auxiliary rectilinear 2D lattices and the 2D lattice of the sheared 3D lattice, and wherein a series of auxiliary 1D lattices of the auxiliary rectilinear 3D lattice is orthogonal to the 2D planes spanned by the 2D lattices, and wherein the lattice constant of the auxiliary 1D lattice is determined as the distance between neighboring 2D planes, wherein the neighboring 2D planes are specified by passing through neighboring ones of the lattice points along the sheared 1D lattice;

determine, for any of the lattice points of the sheared 3D lattice, a nearest one of the lattice points on the constructed auxiliary rectilinear 3D lattice, wherein the nearest lattice point is determined as a coordinate distance between the lattice point of the sheared 3D lattice and any lattice point on the constructed auxiliary rectilinear 3D lattice and the lattice point with the minimal coordinate distance to the lattice point of the sheared 3D lattice is selected, among the lattice points on the constructed auxiliary rectilinear 3D lattice;

assign, for any of the lattice points of the sheared 3D lattice, the value of the scalar field of the lattice point of the sheared 3D lattice to the determined nearest lattice point on the constructed auxiliary rectilinear 3D lattice;

apply, to any of the lattice points of the constructed auxiliary rectilinear 3D lattice, a Euclidean distance transform (EDT) to the value of the scalar field assigned to the lattice point of the constructed auxiliary rectilinear 3D lattice and obtain an associated EDT value of the scalar field;

assign, to any of the lattice points of the sheared 3D lattice, the obtained associated EDT value of the scalar field of the determined nearest lattice point on the constructed auxiliary rectilinear 3D lattice; and render a medical image based on the assigned EDT values of the sheared volume.

16. The system of claim 15, further comprising:

one or more medical scanners configured to provide the volumetric medical dataset to the interface; and a display device configured to receive the rendered medical image, wherein the display device is further configured to display the received medical image.

17. A non-transitory computer-readable medium on which a program is stored, which program can be read and executed by a computer to render a medical image associated with a volumetric medical dataset comprising a sheared volume, when the program comprises instructions for:

receiving the volumetric medical dataset from a medical scanner, wherein the medical scanner provides the volumetric medical dataset according to the sheared volume, wherein the sheared volume is represented by a sheared three-dimensional (3D) lattice comprising a series of parallel rectilinear two-dimensional (2D) lattices and a series of parallel sheared one-dimensional (1D) lattices, wherein each sheared 1D lattice is non-orthogonal to a 2D plane spanned by any one of the 2D lattices, and wherein each lattice point of the sheared 3D lattice represents a voxel of the volumetric medical dataset, wherein a value of a scalar field is associated with the voxel;

constructing an auxiliary rectilinear volume represented by an auxiliary rectilinear 3D lattice, wherein the auxiliary rectilinear volume comprises the sheared volume of the received volumetric medical dataset, wherein a series of auxiliary rectilinear 2D lattices of the auxiliary rectilinear 3D lattice spans the same series of 2D planes as the series of 2D lattice of the sheared 3D lattice with identical 2D lattice constants of the auxiliary rectilinear 2D lattices and the 2D lattice of the sheared 3D lattice, and wherein a series of auxiliary 1D lattices of the auxiliary rectilinear 3D lattice is orthogonal to the 2D planes spanned by the 2D lattices, and wherein a lattice constant of the auxiliary 1D lattice is determined as the distance between neighboring 2D planes, wherein the neighboring 2D planes are specified by passing through neighboring lattice points along the sheared 1D lattice;

determining, for any of the lattice points of the sheared 3D lattice, a nearest lattice point on the constructed auxiliary rectilinear 3D lattice, wherein determining the nearest lattice point comprises determining a coordinate distance between the lattice point of the sheared 3D lattice and any lattice point on the constructed auxiliary rectilinear 3D lattice and selecting the lattice point with the minimal coordinate distance to the lattice point of the sheared 3D lattice, among the lattice points on the constructed auxiliary rectilinear 3D lattice;

assigning, for any of the lattice points of the sheared 3D lattice, the value of the scalar field of the lattice point of the sheared 3D lattice to the determined nearest lattice point on the constructed auxiliary rectilinear 3D lattice;

applying, for any of the lattice points of the constructed auxiliary rectilinear 3D lattice, a Euclidean distance transform (EDT) to the value of the scalar field assigned to the lattice point of the constructed auxiliary rectilinear 3D lattice and obtaining an associated EDT value of the scalar field;

assigning, to any of the lattice points of the sheared 3D lattice, the obtained associated EDT value of the scalar field of the determined nearest lattice point on the constructed auxiliary rectilinear 3D lattice; and rendering a medical image based on the assigned EDT values of the sheared volume.

* * * * *